(12) United States Patent
Diao et al.

(10) Patent No.: US 10,066,244 B2
(45) Date of Patent: Sep. 4, 2018

(54) PROCESS FOR PRODUCING ETHANOL AND FERMENTING ORGANISMS

(71) Applicant: Novozymes A/S, Bagsvaerd (DK)

(72) Inventors: Liuyang Diao, Shanghai (CN); Kate Brandon Sutton, Raleigh, NC (US); Yu Jiang, Shanghai (CN); Sheng Yang, Shanghai (CN); Yingmiao Liu, Shanghai (CN); Fenghui Qian, Shanghai (CN)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/513,880

(22) PCT Filed: Sep. 22, 2015

(86) PCT No.: PCT/CN2015/090204
§ 371 (c)(1),
(2) Date: Mar. 23, 2017

(87) PCT Pub. No.: WO2016/045569
PCT Pub. Date: Mar. 31, 2016

(65) Prior Publication Data
US 2017/0298394 A1 Oct. 19, 2017

(30) Foreign Application Priority Data

Sep. 23, 2014 (WO) ............... PCT/CN2014/087191
Dec. 11, 2014 (WO) ............... PCT/CN2014/093589
Apr. 27, 2015 (WO) ............... PCT/CN2015/077496

(51) Int. Cl.
| | |
|---|---|
| *C12P 7/06* | (2006.01) |
| *C12N 1/14* | (2006.01) |
| *C12P 7/14* | (2006.01) |
| *C12R 1/865* | (2006.01) |
| *C12N 9/90* | (2006.01) |
| *C07K 14/395* | (2006.01) |
| *C12N 9/12* | (2006.01) |
| *C12N 9/10* | (2006.01) |

(52) U.S. Cl.
CPC .............. *C12P 7/14* (2013.01); *C07K 14/395* (2013.01); *C12N 9/1022* (2013.01); *C12N 9/1205* (2013.01); *C12N 9/90* (2013.01); *C12R 1/865* (2013.01); *C12Y 202/01001* (2013.01); *C12Y 202/01002* (2013.01); *C12Y 207/01017* (2013.01); *C12Y 501/03001* (2013.01); *C12Y 503/01005* (2013.01); *C12Y 503/01006* (2013.01)

(58) Field of Classification Search
CPC .................................. C12N 9/1205; C12P 7/46
USPC ..................................... 435/161, 233, 254.21
See application file for complete search history.

(56) References Cited

U.S. PATENT DOCUMENTS 8,586,336 B2 * 11/2013 Bao .................. C12N 9/92
435/106

FOREIGN PATENT DOCUMENTS

| WO | 2003062430 A1 | 7/2003 |
|---|---|---|
| WO | 2009003167 A1 | 12/2008 |

OTHER PUBLICATIONS

Diao et al, 2013, BMC Biotechnology 13, 1-9.
Leandro et al, 2006, Biochem J 395, 543-549.
Leandro et al, 2006, EMBL Accession No. AJ937350.
Runquist et al, 2009, Appl Microbiol Biotechnol 82, 123-130.

* cited by examiner

*Primary Examiner* — Tekchand Saidha
(74) *Attorney, Agent, or Firm* — Eric J. Fechter

(57) ABSTRACT

Processes for producing ethanol comprise saccharifying cellulosic material with a cellulolytic enzyme composition and fermenting the saccharified cellulosic material with a fermenting microorganism to produce ethanol. The fermenting organism is *Saccharomyces cerevisiae* CIBTS1260 (deposited under Accession No. NRRL Y-50973 at the Agricultural Research Service Culture Collection (NRRL), Illinois 61604 U.S.A.) or a fermenting organism that has properties that the same or about the same as that of *Saccharomyces cerevisiae* CIBTS1260).

10 Claims, 7 Drawing Sheets

Specification includes a Sequence Listing.

SEQUENCE LISTING

<160> NUMBER OF SEQ ID NOS: 22

<210> SEQ ID NO 1
<211> LENGTH: 797
<212> TYPE: PRT

<213> ORGANISM: Trichoderma reesei

<400> SEQUENCE: 1

```
Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
        115                 120                 125

Ala Thr Ser Phe Pro Met Pro Ile Leu Thr Thr Ala Ala Leu Asn Arg
    130                 135                 140

Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
        195                 200                 205

Gly Ile Gln Gly Gly Val Asp Pro Glu His Leu Lys Val Ala Ala Thr
    210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Ala Arg Tyr Ala Lys Ser Arg Ser
            260                 265                 270

Leu Met Cys Ala Tyr Asn Ser Val Asn Gly Val Pro Ser Cys Ala Asn
        275                 280                 285

Ser Phe Phe Leu Gln Thr Leu Leu Arg Glu Ser Trp Gly Phe Pro Glu
    290                 295                 300

Trp Gly Tyr Val Ser Ser Asp Cys Asp Ala Val Tyr Asn Val Phe Asn
305                 310                 315                 320

Pro His Asp Tyr Ala Ser Asn Gln Ser Ser Ala Ala Ala Ser Ser Leu
                325                 330                 335

Arg Ala Gly Thr Asp Ile Asp Cys Gly Gln Thr Tyr Pro Trp His Leu
            340                 345                 350

Asn Glu Ser Phe Val Ala Gly Glu Val Ser Arg Gly Glu Ile Glu Arg
        355                 360                 365

Ser Val Thr Arg Leu Tyr Ala Asn Leu Val Arg Leu Gly Tyr Phe Asp
    370                 375                 380

Lys Lys Asn Gln Tyr Arg Ser Leu Gly Trp Lys Asp Val Val Lys Thr
385                 390                 395                 400
```

```
Asp Ala Trp Asn Ile Ser Tyr Glu Ala Ala Val Glu Gly Ile Val Leu
                405                 410                 415

Leu Lys Asn Asp Gly Thr Leu Pro Leu Ser Lys Lys Val Arg Ser Ile
            420                 425                 430

Ala Leu Ile Gly Pro Trp Ala Asn Ala Thr Thr Gln Met Gln Gly Asn
        435                 440                 445

Tyr Tyr Gly Pro Ala Pro Tyr Leu Ile Ser Pro Leu Glu Ala Ala Lys
    450                 455                 460

Lys Ala Gly Tyr His Val Asn Phe Glu Leu Thr Glu Ile Ala Gly
465                 470                 475                 480

Asn Ser Thr Thr Gly Phe Ala Lys Ala Ile Ala Ala Lys Lys Ser
                485                 490                 495

Asp Ala Ile Ile Tyr Leu Gly Gly Ile Asp Asn Thr Ile Glu Gln Glu
            500                 505                 510

Gly Ala Asp Arg Thr Asp Ile Ala Trp Pro Gly Asn Gln Leu Asp Leu
        515                 520                 525

Ile Lys Gln Leu Ser Glu Val Gly Lys Pro Leu Val Val Leu Gln Met
    530                 535                 540

Gly Gly Gly Gln Val Asp Ser Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile
    610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
        675                 680                 685

Lys Thr Glu Ser Pro Tyr Thr Ala Met Leu Phe Val Arg Thr Ser Asn
    690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
                725                 730                 735

Pro Val Ser Ala Leu Ala Arg Val Asp Ser His Gly Asn Arg Ile Val
            740                 745                 750

Tyr Pro Gly Lys Tyr Glu Leu Ala Leu Asn Thr Asp Glu Ser Val Lys
        755                 760                 765

Leu Glu Phe Glu Leu Val Gly Glu Val Thr Ile Glu Asn Trp Pro
    770                 775                 780

Leu Glu Glu Gln Gln Ile Lys Asp Ala Thr Pro Asp Ala
785                 790                 795

<210> SEQ ID NO 2
<211> LENGTH: 452
<212> TYPE: PRT
```

<213> ORGANISM: Thielavia terrestris

<400> SEQUENCE: 2

```
Met Leu Ala Asn Gly Ala Ile Val Phe Leu Ala Ala Leu Gly Val
1               5                   10                  15

Ser Gly His Tyr Thr Trp Pro Arg Val Asn Asp Gly Ala Asp Trp Gln
                20                  25                  30

Gln Val Arg Lys Ala Asp Asn Trp Gln Asp Asn Gly Tyr Val Gly Asp
            35                  40                  45

Val Thr Ser Pro Gln Ile Arg Cys Phe Gln Ala Thr Pro Ser Pro Ala
        50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys Met Leu Ala Asn Gly Ala Ile Val Phe Leu Ala Ala Leu
225                 230                 235                 240

Gly Val Ser Gly His Tyr Thr Trp Pro Arg Val Asn Asp Gly Ala Asp
                245                 250                 255

Trp Gln Gln Val Arg Lys Ala Asp Asn Trp Gln Asp Asn Gly Tyr Val
            260                 265                 270

Gly Asp Val Thr Ser Pro Gln Ile Arg Cys Phe Gln Ala Thr Pro Ser
        275                 280                 285

Pro Ala Pro Ser Val Leu Asn Thr Thr Ala Gly Ser Thr Val Thr Tyr
290                 295                 300

Trp Ala Asn Pro Asp Val Tyr His Pro Gly Pro Val Gln Phe Tyr Met
305                 310                 315                 320

Ala Arg Val Pro Asp Gly Glu Asp Ile Asn Ser Trp Asn Gly Asp Gly
                325                 330                 335

Ala Val Trp Phe Lys Val Tyr Glu Asp His Pro Thr Phe Gly Ala Gln
            340                 345                 350

Leu Thr Trp Pro Ser Thr Gly Lys Ser Ser Phe Ala Val Pro Ile Pro
        355                 360                 365

Pro Cys Ile Lys Ser Gly Tyr Tyr Leu Leu Arg Ala Glu Gln Ile Gly
    370                 375                 380

Leu His Val Ala Gln Ser Val Gly Gly Ala Gln Phe Tyr Ile Ser Cys
385                 390                 395                 400
```

```
Ala Gln Leu Ser Val Thr Gly Gly Ser Thr Glu Pro Pro Asn Lys
            405                 410                 415

Val Ala Phe Pro Gly Ala Tyr Ala Thr Asp Pro Gly Ile Leu Ile
            420                 425                 430

Asn Ile Tyr Tyr Pro Val Pro Thr Ser Tyr Gln Asn Pro Gly Pro Ala
            435                 440                 445

Val Phe Ser Cys
    450

<210> SEQ ID NO 3
<211> LENGTH: 326
<212> TYPE: PRT
<213> ORGANISM: Aspergillus fumigatus

<400> SEQUENCE: 3

Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
                20                  25                  30

Tyr Gly Ser Gln Cys Val Arg Leu Pro Ala Ser Asn Ser Pro Val Thr
            35                  40                  45

Asn Val Ala Ser Asp Asp Ile Arg Cys Asn Val Gly Thr Ser Arg Pro
        50                  55                  60

Thr Val Lys Cys Pro Val Lys Ala Gly Ser Thr Val Thr Ile Glu Met
65                  70                  75                  80

His Gln Gln Pro Gly Asp Arg Ser Cys Ala Asn Glu Ala Ile Gly Gly
                85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
        115                 120                 125

Trp Ala Lys Asn Pro Ser Gly Ser Thr Gly Asp Asp Asp Tyr Trp Gly
    130                 135                 140

Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ser Ser Gly Gly Ala Gln Phe Tyr Met Ser Cys
            180                 185                 190

Tyr Gln Leu Thr Val Thr Gly Ser Gly Ser Ala Thr Pro Ser Thr Val
        195                 200                 205

Asn Phe Pro Gly Ala Tyr Ser Ala Ser Asp Pro Gly Ile Leu Ile Asn
    210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
            260                 265                 270

Thr Ser Thr Ala Thr Ala Thr Ser Ala Pro Gly Gly Gly Ser Gly
        275                 280                 285

Cys Thr Ala Ala Lys Tyr Gln Gln Cys Gly Gly Thr Gly Tyr Thr Gly
    290                 295                 300

Cys Thr Thr Cys Ala Ser Gly Ser Thr Cys Ser Ala Val Ser Pro Pro
305                 310                 315                 320
```

```
Tyr Tyr Ser Gln Cys Leu
            325

<210> SEQ ID NO 4
<211> LENGTH: 250
<212> TYPE: PRT
<213> ORGANISM: Thermoascus aurantiacus

<400> SEQUENCE: 4

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30

Lys Lys Tyr Tyr Gly Gly Tyr Leu Val Asn Gln Tyr Pro Tyr Met Ser
        35                  40                  45

Asn Pro Pro Glu Val Ile Ala Trp Ser Thr Thr Ala Thr Asp Leu Gly
    50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

Val Glu Leu Gln Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Glu Phe Phe Lys Ile Ala Glu Ser Gly Leu Ile Asn Asp
    130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
    210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250

<210> SEQ ID NO 5
<211> LENGTH: 863
<212> TYPE: PRT
<213> ORGANISM: Aspergillus fumigatus

<400> SEQUENCE: 5

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60
```

-continued

```
Gly Thr Gly Trp Glu Met Asp Arg Cys Val Gly Gln Thr Gly Ser Val
 65                  70                  75                  80

Pro Arg Leu Gly Ile Asn Trp Gly Leu Cys Gly Gln Asp Ser Pro Leu
                 85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
450                 455                 460

Gln Ala Ile Gln Arg Glu Val Ile Ser Asn Gly Gly Asn Val Phe Ala
465                 470                 475                 480
```

Val Thr Asp Asn Gly Ala Leu Ser Gln Met Ala Asp Val Ala Ser Gln
            485                 490                 495

Ser Ser Val Ser Leu Val Phe Val Asn Ala Asp Ser Gly Glu Gly Phe
        500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
        610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
        690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
        770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860

<210> SEQ ID NO 6
<211> LENGTH: 406
<212> TYPE: PRT
<213> ORGANISM: Aspergillus aculeatus

<400> SEQUENCE: 6

```
Met Val Gly Leu Leu Ser Ile Thr Ala Ala Leu Ala Ala Thr Val Leu
1               5                   10                  15

Pro Asn Ile Val Ser Ala Val Gly Leu Asp Gln Ala Ala Val Ala Lys
            20                  25                  30

Gly Leu Gln Tyr Phe Gly Thr Ala Thr Asp Asn Pro Glu Leu Thr Asp
                35                  40                  45

Ile Pro Tyr Val Thr Gln Leu Asn Asn Thr Ala Asp Phe Gly Gln Ile
50                      55                  60

Thr Pro Gly Asn Ser Met Lys Trp Asp Ala Thr Glu Pro Ser Gln Gly
65                  70                  75                  80

Thr Phe Thr Phe Thr Lys Gly Asp Val Ile Ala Asp Leu Ala Glu Gly
                85                  90                  95

Asn Gly Gln Tyr Leu Arg Cys His Thr Leu Val Trp Tyr Asn Gln Leu
                100                 105                 110

Pro Ser Trp Val Thr Ser Gly Thr Trp Thr Asn Ala Thr Leu Thr Ala
            115                 120                 125

Ala Leu Lys Asn His Ile Thr Asn Val Val Ser His Tyr Lys Gly Lys
            130                 135                 140

Cys Leu His Trp Asp Val Val Asn Glu Ala Leu Asn Asp Asp Gly Thr
145                 150                 155                 160

Tyr Arg Thr Asn Ile Phe Tyr Thr Thr Ile Gly Glu Ala Tyr Ile Pro
                165                 170                 175

Ile Ala Phe Ala Ala Ala Ala Ala Asp Pro Asp Ala Lys Leu Phe
                180                 185                 190

Tyr Asn Asp Tyr Asn Leu Glu Tyr Gly Gly Ala Lys Ala Ser Ala
                195                 200                 205

Arg Ala Ile Val Gln Leu Val Lys Asn Ala Gly Ala Lys Ile Asp Gly
210                 215                 220

Val Gly Leu Gln Ala His Phe Ser Val Gly Thr Val Pro Ser Thr Ser
225                 230                 235                 240

Ser Leu Val Ser Val Leu Gln Ser Phe Thr Ala Leu Gly Val Glu Val
                245                 250                 255

Ala Tyr Thr Glu Ala Asp Val Arg Ile Leu Leu Pro Thr Thr Ala Thr
            260                 265                 270

Thr Leu Ala Gln Gln Ser Ser Asp Phe Gln Ala Leu Val Gln Ser Cys
    275                 280                 285

Val Gln Thr Thr Gly Cys Val Gly Phe Thr Ile Trp Asp Trp Thr Asp
    290                 295                 300

Lys Tyr Ser Trp Val Pro Ser Thr Phe Ser Gly Tyr Gly Ala Ala Leu
305                 310                 315                 320

Pro Trp Asp Glu Asn Leu Val Lys Lys Pro Ala Tyr Asn Gly Leu Leu
                325                 330                 335

Ala Gly Met Gly Val Thr Val Thr Thr Thr Thr Thr Thr Thr Thr Ala
                340                 345                 350

Thr Ala Thr Gly Lys Thr Thr Thr Thr Thr Gly Ala Thr Ser Thr
    355                 360                 365

Gly Thr Thr Ala Ala His Trp Gly Gln Cys Gly Gly Leu Asn Trp Ser
    370                 375                 380

Gly Pro Thr Ala Cys Ala Thr Gly Tyr Thr Cys Thr Tyr Val Asn Asp
385                 390                 395                 400

Tyr Tyr Ser Gln Cys Leu
            405
```

<210> SEQ ID NO 7
<211> LENGTH: 253
<212> TYPE: PRT
<213> ORGANISM: Penicillium emersonii

<400> SEQUENCE: 7

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

<210> SEQ ID NO 8
<211> LENGTH: 397
<212> TYPE: PRT
<213> ORGANISM: Aspergillus fumigatus

<400> SEQUENCE: 8

Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Ser Gln Asn Ser Phe Ser
65                  70                  75                  80

```
Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
        115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205

Val Lys Met Ile Lys Ala Tyr Gly Ala Lys Ile Asp Gly Val Gly Leu
    210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
                245                 250                 255

Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Cys Val Ser Thr
        275                 280                 285

Thr Gly Cys Val Gly Val Thr Ile Trp Asp Trp Thr Asp Lys Tyr Ser
    290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
                325                 330                 335

Gly Ala Ser Gly Ser Gly Thr Thr Thr Thr Thr Thr Thr Ser Thr
            340                 345                 350

Thr Thr Gly Gly Thr Asp Pro Thr Gly Val Ala Gln Lys Trp Gly Gln
        355                 360                 365

Cys Gly Gly Ile Gly Trp Thr Gly Pro Thr Thr Cys Val Ser Gly Thr
    370                 375                 380

Thr Cys Gln Lys Leu Asn Asp Trp Tyr Ser Gln Cys Leu
385                 390                 395

<210> SEQ ID NO 9
<211> LENGTH: 792
<212> TYPE: PRT
<213> ORGANISM: Aspergillus fumigatus

<400> SEQUENCE: 9

Met Ala Val Ala Lys Ser Ile Ala Ala Val Leu Val Ala Leu Leu Pro
1               5                   10                  15

Gly Ala Leu Ala Gln Ala Asn Thr Ser Tyr Val Asp Tyr Asn Val Glu
            20                  25                  30

Ala Asn Pro Asp Leu Thr Pro Gln Ser Val Ala Thr Ile Asp Leu Ser
        35                  40                  45

Phe Pro Asp Cys Glu Asn Gly Pro Leu Ser Lys Thr Leu Val Cys Asp
    50                  55                  60
```

Thr Ser Ala Arg Pro His Asp Arg Ala Ala Ala Leu Val Ser Met Phe
 65                  70                  75                  80

Thr Phe Glu Glu Leu Val Asn Asn Thr Gly Asn Thr Ser Pro Gly Val
                 85                  90                  95

Pro Arg Leu Gly Leu Pro Pro Tyr Gln Val Trp Ser Glu Ala Leu His
            100                 105                 110

Gly Leu Asp Arg Ala Asn Phe Thr Asn Glu Gly Glu Tyr Ser Trp Ala
        115                 120                 125

Thr Ser Phe Pro Met Pro Ile Leu Thr Met Ser Ala Leu Asn Arg Thr
130                 135                 140

Leu Ile Asn Gln Ile Ala Thr Ile Ile Ala Thr Gln Gly Arg Ala Phe
145                 150                 155                 160

Asn Asn Val Gly Arg Tyr Gly Leu Asp Val Tyr Ala Pro Asn Ile Asn
                165                 170                 175

Ala Phe Arg Ser Ala Met Trp Gly Arg Gly Gln Glu Thr Pro Gly Glu
            180                 185                 190

Asp Ala Tyr Cys Leu Ala Ser Ala Tyr Ala Tyr Glu Tyr Ile Thr Gly
        195                 200                 205

Ile Gln Gly Gly Val Asp Pro Glu His Leu Lys Leu Val Ala Thr Ala
210                 215                 220

Lys His Tyr Ala Gly Tyr Asp Leu Glu Asn Trp Asp Gly His Ser Arg
225                 230                 235                 240

Leu Gly Asn Asp Met Asn Ile Thr Gln Gln Glu Leu Ser Glu Tyr Tyr
                245                 250                 255

Thr Pro Gln Phe Leu Val Ala Ala Arg Asp Ala Lys Val His Ser Val
            260                 265                 270

Met Cys Ser Tyr Asn Ala Val Asn Gly Val Pro Ser Cys Ala Asn Ser
        275                 280                 285

Phe Phe Leu Gln Thr Leu Leu Arg Asp Thr Phe Gly Phe Val Glu Asp
290                 295                 300

Gly Tyr Val Ser Ser Asp Cys Asp Ser Ala Tyr Asn Val Trp Asn Pro
305                 310                 315                 320

His Glu Phe Ala Ala Asn Ile Thr Gly Ala Ala Ala Asp Ser Ile Arg
                325                 330                 335

Ala Gly Thr Asp Ile Asp Cys Gly Thr Thr Tyr Gln Tyr Tyr Phe Gly
            340                 345                 350

Glu Ala Phe Asp Glu Gln Glu Val Thr Arg Ala Glu Ile Glu Arg Gly
        355                 360                 365

Val Ile Arg Leu Tyr Ser Asn Leu Val Arg Leu Gly Tyr Phe Asp Gly
370                 375                 380

Asn Gly Ser Val Tyr Arg Asp Leu Thr Trp Asn Asp Val Val Thr Thr
385                 390                 395                 400

Asp Ala Trp Asn Ile Ser Tyr Glu Ala Val Glu Gly Ile Val Leu
                405                 410                 415

Leu Lys Asn Asp Gly Thr Leu Pro Leu Ala Lys Ser Val Arg Ser Val
            420                 425                 430

Ala Leu Ile Gly Pro Trp Met Asn Val Thr Thr Gln Leu Gln Gly Asn
        435                 440                 445

Tyr Phe Gly Pro Ala Pro Tyr Leu Ile Ser Pro Leu Asn Ala Phe Gln
450                 455                 460

Asn Ser Asp Phe Asp Val Asn Tyr Ala Phe Gly Thr Asn Ile Ser Ser
465                 470                 475                 480

```
His Ser Thr Asp Gly Phe Ser Glu Ala Leu Ser Ala Ala Lys Lys Ser
                485                 490                 495

Asp Val Ile Ile Phe Ala Gly Gly Ile Asp Asn Thr Leu Glu Ala Glu
            500                 505                 510

Ala Met Asp Arg Met Asn Ile Thr Trp Pro Gly Asn Gln Leu Gln Leu
        515                 520                 525

Ile Asp Gln Leu Ser Gln Leu Gly Lys Pro Leu Ile Val Leu Gln Met
    530                 535                 540

Gly Gly Gly Gln Val Asp Ser Ser Ser Leu Lys Ser Asn Lys Asn Val
545                 550                 555                 560

Asn Ser Leu Ile Trp Gly Gly Tyr Pro Gly Gln Ser Gly Gly Gln Ala
                565                 570                 575

Leu Leu Asp Ile Ile Thr Gly Lys Arg Ala Pro Ala Gly Arg Leu Val
            580                 585                 590

Val Thr Gln Tyr Pro Ala Glu Tyr Ala Thr Gln Phe Pro Ala Thr Asp
        595                 600                 605

Met Ser Leu Arg Pro His Gly Asn Asn Pro Gly Gln Thr Tyr Met Trp
    610                 615                 620

Tyr Thr Gly Thr Pro Val Tyr Glu Phe Gly His Gly Leu Phe Tyr Thr
625                 630                 635                 640

Thr Phe His Ala Ser Leu Pro Gly Thr Gly Lys Asp Lys Thr Ser Phe
                645                 650                 655

Asn Ile Gln Asp Leu Leu Thr Gln Pro His Pro Gly Phe Ala Asn Val
            660                 665                 670

Glu Gln Met Pro Leu Leu Asn Phe Thr Val Thr Ile Thr Asn Thr Gly
        675                 680                 685

Lys Val Ala Ser Asp Tyr Thr Ala Met Leu Phe Ala Asn Thr Thr Ala
    690                 695                 700

Gly Pro Ala Pro Tyr Pro Asn Lys Trp Leu Val Gly Phe Asp Arg Leu
705                 710                 715                 720

Ala Ser Leu Glu Pro His Arg Ser Gln Thr Met Thr Ile Pro Val Thr
                725                 730                 735

Ile Asp Ser Val Ala Arg Thr Asp Glu Ala Gly Asn Arg Val Leu Tyr
            740                 745                 750

Pro Gly Lys Tyr Glu Leu Ala Leu Asn Asn Glu Arg Ser Val Val Leu
        755                 760                 765

Gln Phe Val Leu Thr Gly Arg Glu Ala Val Ile Phe Lys Trp Pro Val
    770                 775                 780

Glu Gln Gln Gln Ile Ser Ser Ala
785                 790

<210> SEQ ID NO 10
<211> LENGTH: 532
<212> TYPE: PRT
<213> ORGANISM: Aspergillus fumigatus

<400> SEQUENCE: 10

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60
```

```
Arg Trp Val His Lys Val Gly Asp Tyr Thr Asn Cys Tyr Thr Gly Asn
 65                  70                  75                  80

Thr Trp Asp Thr Thr Ile Cys Pro Asp Asp Ala Thr Cys Ala Ser Asn
                 85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
465                 470                 475                 480
```

Gln Pro Thr Thr Thr Thr Thr Ala Gly Asn Pro Gly Gly Thr Gly
            485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
            515                 520                 525

Ser Gln Cys Leu
            530

<210> SEQ ID NO 11
<211> LENGTH: 454
<212> TYPE: PRT
<213> ORGANISM: Aspergillus fumigatus

<400> SEQUENCE: 11

Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
50                  55                  60

Leu Thr Thr Thr Ala Ala Thr Thr Thr Ser Gln Thr Thr Thr Thr Lys
65                  70                  75                  80

Pro Thr Thr Thr Gly Pro Thr Thr Ser Ala Pro Thr Val Thr Ala Ser
            85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
            115                 120                 125

Pro Lys Ala Ser Ala Val Ala Glu Val Pro Ser Phe Val Trp Leu Asp
        130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
            165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
            195                 200                 205

Asp Ala Ile Arg Ala Gln Leu Val Lys Tyr Ser Asp Val His Thr Ile
        210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
            245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
            275                 280                 285

Ala Thr Leu Phe Ala Lys Val Tyr Thr Asp Ala Gly Ser Pro Ala Ala
        290                 295                 300

Val Arg Gly Leu Ala Thr Asn Val Ala Asn Tyr Asn Ala Trp Ser Leu
305                 310                 315                 320

```
Ser Thr Cys Pro Ser Tyr Thr Gln Gly Asp Pro Asn Cys Asp Glu Lys
            325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
            355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
            435                 440                 445

Asn Ala Asn Pro Ser Phe
            450

<210> SEQ ID NO 12
<211> LENGTH: 620
<212> TYPE: PRT
<213> ORGANISM: Myceliophthora thermophila

<400> SEQUENCE: 12

Met Lys Ser Phe Ile Ser Ala Ala Thr Leu Leu Val Gly Ile Leu Thr
1               5                   10                  15

Pro Ser Val Ala Ala Ala Pro Pro Ser Thr Pro Glu Gln Arg Asp Leu
            20                  25                  30

Leu Val Pro Ile Thr Glu Arg Glu Ala Ala Val Lys Ala Arg Gln
        35                  40                  45

Gln Ser Cys Asn Thr Pro Ser Asn Arg Ala Cys Trp Thr Asp Gly Tyr
    50                  55                  60

Asp Ile Asn Thr Asp Tyr Glu Val Asp Ser Pro Asp Thr Gly Val Val
65                  70                  75                  80

Arg Pro Tyr Thr Leu Thr Leu Thr Glu Val Asp Asn Trp Thr Gly Pro
                85                  90                  95

Asp Gly Val Val Lys Glu Lys Val Met Leu Val Asn Asn Ser Ile Ile
            100                 105                 110

Gly Pro Thr Ile Phe Ala Asp Trp Gly Asp Thr Ile Gln Val Thr Val
            115                 120                 125

Ile Asn Asn Leu Glu Thr Asn Gly Thr Ser Ile His Trp His Gly Leu
    130                 135                 140

His Gln Lys Gly Thr Asn Leu His Asp Gly Ala Asn Gly Ile Thr Glu
145                 150                 155                 160

Cys Pro Ile Pro Pro Lys Gly Gly Arg Lys Val Tyr Arg Phe Lys Ala
                165                 170                 175

Gln Gln Tyr Gly Thr Ser Trp Tyr His Ser His Phe Ser Ala Gln Tyr
            180                 185                 190

Gly Asn Gly Val Val Gly Ala Ile Gln Ile Asn Gly Pro Ala Ser Leu
            195                 200                 205

Pro Tyr Asp Thr Asp Leu Gly Val Phe Pro Ile Ser Asp Tyr Tyr Tyr
            210                 215                 220

Ser Ser Ala Asp Glu Leu Val Glu Leu Thr Lys Asn Ser Gly Ala Pro
```

```
            225                 230                 235                 240
        Phe Ser Asp Asn Val Leu Phe Asn Gly Thr Ala Lys His Pro Glu Thr
                        245                 250                 255
        Gly Glu Gly Glu Tyr Ala Asn Val Thr Leu Thr Pro Gly Arg Arg His
                        260                 265                 270
        Arg Leu Arg Leu Ile Asn Thr Ser Val Glu Asn His Phe Gln Val Ser
                        275                 280                 285
        Leu Val Asn His Thr Met Cys Ile Ile Ala Ala Asp Met Val Pro Val
                290                 295                 300
        Asn Ala Met Thr Val Asp Ser Leu Phe Leu Gly Val Gly Gln Arg Tyr
        305                 310                 315                 320
        Asp Val Val Ile Glu Ala Asn Arg Thr Pro Gly Asn Tyr Trp Phe Asn
                        325                 330                 335
        Val Thr Phe Gly Gly Leu Leu Cys Gly Gly Ser Arg Asn Pro Tyr
                        340                 345                 350
        Pro Ala Ala Ile Phe His Tyr Ala Gly Ala Pro Gly Gly Pro Pro Thr
                        355                 360                 365
        Asp Glu Gly Lys Ala Pro Val Asp His Asn Cys Leu Asp Leu Pro Asn
                370                 375                 380
        Leu Lys Pro Val Val Ala Arg Asp Val Pro Leu Ser Gly Phe Ala Lys
        385                 390                 395                 400
        Arg Ala Asp Asn Thr Leu Asp Val Thr Leu Asp Thr Thr Gly Thr Pro
                        405                 410                 415
        Leu Phe Val Trp Lys Val Asn Gly Ser Ala Ile Asn Ile Asp Trp Gly
                        420                 425                 430
        Arg Ala Val Val Asp Tyr Val Leu Thr Gln Asn Thr Ser Phe Pro Pro
                        435                 440                 445
        Gly Tyr Asn Ile Val Glu Val Asn Gly Ala Asp Gln Trp Ser Tyr Trp
                        450                 455                 460
        Leu Ile Glu Asn Asp Pro Gly Ala Pro Phe Thr Leu Pro His Pro Met
        465                 470                 475                 480
        His Leu His Gly His Asp Phe Tyr Val Leu Gly Arg Ser Pro Asp Glu
                        485                 490                 495
        Ser Pro Ala Ser Asn Glu Arg His Val Phe Asp Pro Ala Arg Asp Ala
                        500                 505                 510
        Gly Leu Leu Ser Gly Ala Asn Pro Val Arg Arg Asp Val Ser Met Leu
                        515                 520                 525
        Pro Ala Phe Gly Trp Val Val Leu Ser Phe Arg Ala Asp Asn Pro Gly
                530                 535                 540
        Ala Trp Leu Phe His Cys His Ile Ala Trp His Val Ser Gly Gly Leu
        545                 550                 555                 560
        Gly Val Val Tyr Leu Glu Arg Ala Asp Asp Leu Arg Gly Ala Val Ser
                        565                 570                 575
        Asp Ala Asp Ala Asp Asp Leu Asp Arg Leu Cys Ala Asp Trp Arg Arg
                        580                 585                 590
        Tyr Trp Pro Thr Asn Pro Tyr Pro Lys Ser Asp Ser Gly Leu Lys His
                        595                 600                 605
        Arg Trp Val Glu Glu Gly Glu Trp Leu Val Lys Ala
                610                 615                 620

<210> SEQ ID NO 13
<211> LENGTH: 439
<212> TYPE: PRT
<213> ORGANISM: Artificial Sequence
```

<220> FEATURE:
<223> OTHER INFORMATION: Bovine Xylose Isomerase disclosed in US8586336B

<400> SEQUENCE: 13

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Glu Pro Glu Lys
            20                  25                  30

Val Val Met Gly Lys Lys Met Lys Asp Trp Leu Lys Phe Ala Met Ala
            35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Glu Cys Pro Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Ala Pro Thr
            100                 105                 110

Ile Ala Glu Tyr Glu Glu Arg Met Lys Ala Ile Thr Asp Tyr Ala Gln
            115                 120                 125

Glu Lys Met Lys Gln Phe Pro Asn Ile Lys Leu Leu Trp Gly Thr Ala
130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ser Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
            195                 200                 205

Glu His Met Ala Thr Met Leu Gly Met Ala Arg Asp Tyr Ala Arg Ala
210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
            275                 280                 285

Val Asp Ala Gly Met Leu Gly Ser Ile Asp Ala Asn Arg Gly Asp Ala
290                 295                 300

Gln Asn Gly Trp Asp Thr Asp Gln Phe Pro Ile Asp Asn Phe Glu Leu
305                 310                 315                 320

Thr Gln Ala Met Leu Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
            355                 360                 365

Leu Met Asn Ala Ala Asp Ile Leu Glu Asn Ser Glu Leu Pro Ala Met
370                 375                 380

Lys Lys Ala Arg Tyr Ala Ser Phe Asp Ser Gly Ile Gly Lys Asp Phe
385                 390                 395                 400
```

```
Glu Asp Gly Lys Leu Thr Phe Glu Gln Val Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu His Cys Lys
        435

<210> SEQ ID NO 14
<211> LENGTH: 507
<212> TYPE: PRT
<213> ORGANISM: Talaromyces leycettanus

<400> SEQUENCE: 14

Gln Gln Ala Gly Thr Leu Thr Thr Glu Thr His Pro Ser Leu Thr Trp
1               5                   10                  15

Gln Gln Cys Ser Ala Gly Gly Ser Cys Thr Thr Gln Asn Gly Lys Val
                20                  25                  30

Val Ile Asp Ala Asn Trp Arg Trp Val His Ser Thr Ser Gly Ser Asn
            35                  40                  45

Asn Cys Tyr Thr Gly Asn Thr Trp Asp Ala Thr Leu Cys Pro Asp Asp
        50                  55                  60

Val Thr Cys Ala Ala Asn Cys Ala Leu Asp Gly Ala Asp Tyr Ser Gly
65                  70                  75                  80

Thr Tyr Gly Val Thr Thr Ser Gly Asn Ser Leu Arg Leu Asn Phe Val
                85                  90                  95

Thr Gln Ala Ser Gln Lys Asn Val Gly Ser Arg Leu Tyr Leu Met Glu
            100                 105                 110

Asn Asp Thr Thr Tyr Gln Ile Phe Lys Leu Leu Asn Gln Glu Phe Thr
        115                 120                 125

Phe Asp Val Asp Val Ser Asn Leu Pro Cys Gly Leu Asn Gly Ala Leu
130                 135                 140

Tyr Leu Val Ala Met Asp Ala Asp Gly Gly Met Ala Lys Tyr Pro Thr
145                 150                 155                 160

Asn Lys Ala Gly Ala Lys Tyr Gly Thr Gly Tyr Cys Asp Ser Gln Cys
                165                 170                 175

Pro Arg Asp Leu Lys Phe Ile Asn Gly Glu Ala Asn Val Glu Gly Trp
            180                 185                 190

Gln Pro Ser Ser Asn Asp Pro Asn Ser Gly Ile Gly Asn His Gly Ser
        195                 200                 205

Cys Cys Ala Glu Met Asp Ile Trp Glu Ala Asn Ser Ile Ser Asn Ala
210                 215                 220

Val Thr Pro His Pro Cys Asp Thr Pro Gly Gln Val Met Cys Thr Gly
225                 230                 235                 240

Asn Asn Cys Gly Gly Thr Tyr Ser Thr Thr Arg Tyr Ala Gly Thr Cys
                245                 250                 255

Asp Pro Asp Gly Cys Asp Phe Asn Pro Tyr Arg Met Gly Asn His Ser
            260                 265                 270

Phe Tyr Gly Pro Lys Gln Ile Val Asp Thr Ser Ser Lys Phe Thr Val
        275                 280                 285

Val Thr Gln Phe Leu Thr Asp Asp Gly Thr Ser Thr Gly Thr Leu Ser
290                 295                 300

Glu Ile Arg Arg Phe Tyr Val Gln Asn Gly Gln Val Ile Pro Asn Ser
305                 310                 315                 320

Val Ser Thr Ile Ser Gly Val Ser Gly Asn Ser Ile Thr Thr Glu Phe
```

```
                325                 330                 335
Cys Thr Ala Gln Lys Gln Ala Phe Gly Asp Thr Asp Asp Phe Ser Lys
                340                 345                 350

His Gly Gly Leu Ser Gly Met Ser Ala Ala Leu Ser Gln Gly Met Val
            355                 360                 365

Leu Val Met Ser Leu Trp Asp Asp His Ala Ala Asn Met Leu Trp Leu
370                 375                 380

Asp Ser Thr Tyr Pro Thr Asn Ala Thr Ser Ser Thr Pro Gly Ala Ala
385                 390                 395                 400

Arg Gly Thr Cys Asp Ile Ser Ser Gly Val Pro Ala Asp Val Glu Ser
                405                 410                 415

Asn Asp Pro Asn Ala Tyr Val Val Tyr Ser Asn Ile Lys Val Gly Pro
            420                 425                 430

Ile Gly Ser Thr Phe Ser Ser Ser Gly Ser Gly Ser Ser Ser Ser Ser
        435                 440                 445

Ser Thr Thr Thr Thr Thr Thr Ala Ser Pro Thr Thr Thr Thr Ser Ser
450                 455                 460

Ala Ser Ser Thr Gly Thr Gly Val Ala Gln His Trp Gly Gln Cys Gly
465                 470                 475                 480

Gly Gln Gly Trp Thr Gly Pro Thr Thr Cys Val Ser Pro Tyr Thr Cys
                485                 490                 495

Gln Glu Leu Asn Pro Tyr Tyr Tyr Gln Cys Leu
            500                 505

<210> SEQ ID NO 15
<211> LENGTH: 507
<212> TYPE: PRT
<213> ORGANISM: Talaromyces leycettanus

<400> SEQUENCE: 15

Gln Gln Ala Gly Thr Leu Thr Thr Glu Thr His Pro Ser Leu Thr Trp
1               5                   10                  15

Gln Gln Cys Ser Ala Gly Gly Ser Cys Thr Thr Gln Asn Gly Lys Val
                20                  25                  30

Val Ile Asp Ala Asn Trp Arg Trp Val His Ser Thr Ser Gly Ser Asn
            35                  40                  45

Asn Cys Tyr Thr Gly Asn Thr Trp Asp Ala Thr Leu Cys Pro Asp Asp
        50                  55                  60

Val Thr Cys Ala Ala Asn Cys Ala Leu Asp Gly Ala Asp Tyr Ser Gly
65                  70                  75                  80

Thr Tyr Gly Val Thr Thr Ser Gly Asn Ser Leu Arg Leu Asn Phe Val
                85                  90                  95

Thr Gln Ala Ser Gln Lys Asn Val Gly Ser Arg Leu Tyr Leu Met Glu
            100                 105                 110

Asn Asp Thr Thr Tyr Gln Ile Phe Lys Leu Leu Asn Gln Glu Phe Thr
        115                 120                 125

Phe Asp Val Asp Val Ser Asn Leu Pro Cys Gly Leu Asn Gly Ala Leu
130                 135                 140

Tyr Leu Val Ala Met Asp Ala Asp Gly Gly Met Ala Lys Tyr Pro Thr
145                 150                 155                 160

Asn Lys Ala Gly Ala Lys Tyr Gly Thr Gly Tyr Cys Asp Ser Gln Cys
                165                 170                 175

Pro Arg Asp Leu Lys Phe Ile Asn Gly Glu Ala Asn Val Glu Gly Trp
            180                 185                 190
```

```
Gln Pro Ser Ser Asn Asp Pro Asn Ser Gly Ile Gly Asn His Gly Ser
            195                 200                 205

Cys Cys Ala Glu Met Asp Ile Trp Glu Ala Asn Ser Ile Ser Asn Ala
210                 215                 220

Val Thr Pro His Pro Cys Asp Thr Pro Gly Gln Val Met Cys Thr Gly
225                 230                 235                 240

Asn Asn Cys Gly Gly Thr Tyr Ser Thr Thr Arg Tyr Ala Gly Thr Cys
                245                 250                 255

Asp Pro Asp Gly Cys Asp Phe Asn Pro Tyr Arg Met Gly Asn His Ser
            260                 265                 270

Phe Tyr Gly Pro Lys Gln Ile Val Asp Thr Ser Ser Lys Phe Thr Val
            275                 280                 285

Val Thr Gln Phe Leu Thr Asp Asp Gly Thr Ser Thr Gly Thr Leu Ser
290                 295                 300

Glu Ile Arg Arg Phe Tyr Val Gln Asn Gly Gln Val Ile Pro Asn Ser
305                 310                 315                 320

Val Ser Thr Ile Ser Gly Val Ser Gly Asn Ser Ile Thr Thr Glu Phe
                325                 330                 335

Cys Thr Ala Gln Lys Gln Ala Phe Gly Asp Thr Asp Asp Phe Ser Lys
                340                 345                 350

His Gly Gly Leu Ser Gly Met Ser Ala Ala Leu Ser Gln Gly Met Val
            355                 360                 365

Leu Val Met Ser Leu Trp Asp Asp His Ala Ala Asn Met Leu Trp Leu
            370                 375                 380

Asp Ser Thr Tyr Pro Thr Asn Ala Thr Ser Ser Thr Pro Gly Ala Ala
385                 390                 395                 400

Arg Gly Thr Cys Asp Ile Ser Ser Gly Val Pro Ala Asp Val Glu Ser
                405                 410                 415

Asn Asp Pro Asn Ala Tyr Val Val Tyr Ser Asn Ile Lys Val Gly Pro
            420                 425                 430

Ile Gly Ser Thr Phe Ser Ser Gly Ser Gly Ser Ser Ser Ser Ser Ser
            435                 440                 445

Ser Thr Thr Thr Thr Thr Ala Ser Pro Thr Thr Thr Thr Ser Ser
450                 455                 460

Ala Ser Ser Thr Gly Thr Gly Val Ala Gln His Trp Gly Gln Cys Gly
465                 470                 475                 480

Gly Gln Gly Trp Thr Gly Pro Thr Thr Cys Val Ser Pro Tyr Thr Cys
            485                 490                 495

Gln Glu Leu Asn Pro Tyr Tyr Tyr Gln Cys Leu
            500                 505

<210> SEQ ID NO 16
<211> LENGTH: 385
<212> TYPE: PRT
<213> ORGANISM: Talaromyces leycettanus

<400> SEQUENCE: 16

Ala Gly Leu Asn Thr Ala Ala Lys Ala Ile Gly Lys Leu Tyr Phe Gly
1                   5                   10                  15

Thr Ala Thr Asp Asn Pro Glu Leu Ser Asp Ser Thr Tyr Met Gln Glu
                20                  25                  30

Thr Asp Asn Thr Asp Asp Phe Gly Gln Leu Thr Pro Ala Asn Ser Met
            35                  40                  45

Lys Trp Asp Ala Thr Glu Pro Ser Gln Asn Thr Phe Phe Thr Asn
50                  55                  60
```

Gly Asp Gln Ile Ala Asn Leu Ala Lys Ser Asn Gly Gln Met Leu Arg
65                  70                  75                  80

Cys His Asn Leu Val Trp Tyr Asn Gln Leu Pro Ser Trp Val Thr Ser
                85                  90                  95

Gly Ser Trp Thr Asn Ala Thr Leu Leu Ala Ala Met Lys Asn His Ile
            100                 105                 110

Thr Asn Val Val Thr His Tyr Lys Gly Gln Cys Tyr Ala Trp Asp Val
        115                 120                 125

Val Asn Glu Ala Leu Asn Asp Asp Gly Thr Tyr Arg Ser Asn Val Phe
130                 135                 140

Tyr Gln Tyr Ile Gly Glu Ala Tyr Ile Pro Ile Ala Phe Ala Thr Ala
145                 150                 155                 160

Ala Ala Ala Asp Pro Asn Ala Lys Leu Tyr Tyr Asn Asp Tyr Asn Ile
                165                 170                 175

Glu Tyr Pro Gly Ala Lys Ala Thr Ala Ala Gln Asn Ile Val Lys Met
            180                 185                 190

Val Lys Ala Tyr Gly Ala Lys Ile Asp Gly Val Gly Leu Gln Ser His
        195                 200                 205

Phe Ile Val Gly Ser Thr Pro Ser Gln Ser Ser Gln Ser Asn Met
210                 215                 220

Ala Ala Phe Thr Ala Leu Gly Val Glu Val Ala Ile Thr Glu Leu Asp
225                 230                 235                 240

Ile Arg Met Thr Leu Pro Ser Thr Ser Ala Leu Leu Ala Gln Gln Ser
                245                 250                 255

Thr Asp Tyr Gln Ser Thr Val Ser Ala Cys Val Asn Thr Pro Lys Cys
            260                 265                 270

Ile Gly Ile Thr Leu Trp Asp Trp Thr Asp Lys Tyr Ser Trp Val Pro
        275                 280                 285

Asn Thr Phe Ser Gly Gln Gly Asp Ala Cys Pro Trp Asp Ser Asn Tyr
290                 295                 300

Gln Lys Lys Pro Ala Tyr Tyr Gly Ile Leu Thr Ala Leu Gly Gly Ser
305                 310                 315                 320

Ala Ser Thr Ser Thr Thr Thr Leu Val Thr Ser Arg Thr Ser
                325                 330                 335

Thr Thr Thr Ser Thr Ser Ala Thr Ser Thr Ser Thr Gly Val Ala Gln
            340                 345                 350

His Trp Gly Gln Cys Gly Gly Ile Gly Trp Thr Gly Pro Thr Thr Cys
        355                 360                 365

Ala Ser Pro Tyr Thr Cys Gln Glu Leu Asn Pro Tyr Tyr Tyr Gln Cys
        370                 375                 380

Leu
385

<210> SEQ ID NO 17
<211> LENGTH: 775
<212> TYPE: PRT
<213> ORGANISM: Talaromyces emersonii

<400> SEQUENCE: 17

Gln Asp Asn Gln Thr Tyr Ala Asn Tyr Ser Ser Gln Ser Gln Pro Asp
1               5                   10                  15

Leu Phe Pro Arg Thr Val Ala Thr Ile Asp Leu Ser Phe Pro Asp Cys
                20                  25                  30

Glu Asn Gly Pro Leu Ser Thr Asn Leu Val Cys Asn Lys Ser Ala Asp

```
              35                  40                  45
Pro Trp Ala Arg Ala Glu Ala Leu Ile Ser Leu Phe Thr Leu Glu Glu
 50                  55                  60

Leu Ile Asn Asn Thr Gln Asn Thr Ala Pro Gly Val Pro Arg Leu Gly
 65                  70                  75                  80

Leu Pro Gln Tyr Gln Val Trp Asn Glu Ala Leu His Gly Leu Asp Arg
                 85                  90                  95

Ala Asn Phe Ser His Ser Gly Glu Tyr Ser Trp Ala Thr Ser Phe Pro
                100                 105                 110

Met Pro Ile Leu Ser Met Ala Ser Phe Asn Arg Thr Leu Ile Asn Gln
                115                 120                 125

Ile Ala Ser Ile Ile Ala Thr Gln Ala Arg Ala Phe Asn Asn Ala Gly
                130                 135                 140

Arg Tyr Gly Leu Asp Ser Tyr Ala Pro Asn Ile Asn Gly Phe Arg Ser
145                 150                 155                 160

Pro Leu Trp Gly Arg Gly Gln Glu Thr Pro Gly Glu Asp Ala Phe Phe
                165                 170                 175

Leu Ser Ser Thr Tyr Ala Tyr Glu Tyr Ile Thr Gly Leu Gln Gly Gly
                180                 185                 190

Val Asp Pro Glu His Val Lys Ile Val Ala Thr Ala Lys His Phe Ala
                195                 200                 205

Gly Tyr Asp Leu Glu Asn Trp Gly Asn Val Ser Arg Leu Gly Phe Asn
                210                 215                 220

Ala Ile Ile Thr Gln Gln Asp Leu Ser Glu Tyr Tyr Thr Pro Gln Phe
225                 230                 235                 240

Leu Ala Ser Ala Arg Tyr Ala Lys Thr Arg Ser Ile Met Cys Ser Tyr
                245                 250                 255

Asn Ala Val Asn Gly Val Pro Ser Cys Ala Asn Ser Phe Phe Leu Gln
                260                 265                 270

Thr Leu Leu Arg Glu Asn Phe Asp Phe Val Asp Asp Gly Tyr Val Ser
                275                 280                 285

Ser Asp Cys Asp Ala Val Tyr Asn Val Phe Asn Pro His Gly Tyr Ala
                290                 295                 300

Leu Asn Gln Ser Gly Ala Ala Asp Ser Leu Leu Ala Gly Thr Asp
305                 310                 315                 320

Ile Asp Cys Gly Gln Thr Leu Pro Trp His Leu Asn Glu Ser Phe Val
                325                 330                 335

Glu Gly Tyr Val Ser Arg Gly Asp Ile Glu Lys Ser Leu Thr Arg Leu
                340                 345                 350

Tyr Ser Asn Leu Val Arg Leu Gly Tyr Phe Asp Gly Asn Asn Ser Glu
                355                 360                 365

Tyr Arg Asn Leu Asn Trp Asn Asp Val Val Thr Thr Asp Ala Trp Asn
                370                 375                 380

Ile Ser Tyr Glu Ala Ala Val Glu Gly Ile Thr Leu Leu Lys Asn Asp
385                 390                 395                 400

Gly Thr Leu Pro Leu Ser Lys Lys Val Arg Ser Ile Ala Leu Ile Gly
                405                 410                 415

Pro Trp Ala Asn Ala Thr Val Gln Met Gln Gly Asn Tyr Tyr Gly Thr
                420                 425                 430

Pro Pro Tyr Leu Ile Ser Pro Leu Glu Ala Ala Lys Ala Ser Gly Phe
                435                 440                 445

Thr Val Asn Tyr Ala Phe Gly Thr Asn Ile Ser Thr Asp Ser Thr Gln
                450                 455                 460
```

```
Trp Phe Ala Glu Ala Ile Ala Ala Ala Lys Lys Ser Asp Val Ile Ile
465                 470                 475                 480

Tyr Ala Gly Gly Ile Asp Asn Thr Ile Glu Ala Gly Gln Asp Arg
                485                 490                 495

Thr Asp Leu Lys Trp Pro Gly Asn Gln Leu Asp Leu Ile Glu Gln Leu
            500                 505                 510

Ser Gln Val Gly Lys Pro Leu Val Leu Gln Met Gly Gly Gln
            515                 520                 525

Val Asp Ser Ser Ser Leu Lys Ala Asn Lys Asn Val Asn Ala Leu Val
    530                 535                 540

Trp Gly Gly Tyr Pro Gly Gln Ser Gly Gly Ala Ala Leu Phe Asp Ile
545                 550                 555                 560

Leu Thr Gly Lys Arg Ala Pro Ala Gly Arg Leu Val Ser Thr Gln Tyr
                565                 570                 575

Pro Ala Glu Tyr Ala Thr Gln Phe Pro Ala Asn Asp Met Asn Leu Arg
            580                 585                 590

Pro Asn Gly Ser Asn Pro Gly Gln Thr Tyr Ile Trp Tyr Thr Gly Thr
            595                 600                 605

Pro Val Tyr Glu Phe Gly His Gly Leu Phe Tyr Thr Glu Phe Gln Glu
        610                 615                 620

Ser Ala Ala Ala Gly Thr Asn Lys Thr Ser Thr Phe Asp Ile Leu Asp
625                 630                 635                 640

Leu Phe Ser Thr Pro His Pro Gly Tyr Glu Tyr Ile Glu Gln Val Pro
                645                 650                 655

Phe Ile Asn Val Thr Val Asp Val Lys Asn Val Gly His Thr Pro Ser
                660                 665                 670

Pro Tyr Thr Gly Leu Leu Phe Ala Asn Thr Thr Ala Gly Pro Lys Pro
            675                 680                 685

Tyr Pro Asn Lys Trp Leu Val Gly Phe Asp Trp Leu Pro Thr Ile Gln
        690                 695                 700

Pro Gly Glu Thr Ala Lys Leu Thr Ile Pro Val Pro Leu Gly Ala Ile
705                 710                 715                 720

Ala Trp Ala Asp Glu Asn Gly Asn Lys Val Val Phe Pro Gly Asn Tyr
                725                 730                 735

Glu Leu Ala Leu Asn Asn Glu Arg Ser Val Val Ser Phe Thr Leu
            740                 745                 750

Thr Gly Asp Ala Ala Thr Leu Glu Lys Trp Pro Leu Trp Glu Gln Ala
            755                 760                 765

Val Pro Gly Val Leu Gln Gln
    770                 775

<210> SEQ ID NO 18
<211> LENGTH: 1644
<212> TYPE: DNA
<213> ORGANISM: Candida intermedia

<400> SEQUENCE: 18
atgtcacaag actctcactc atcaggtgcc gcaaccccag taaatggtag tatattagaa      60
aaggaaaagg aagactctcc agtattgcaa gtagatgccc acaaaaggg ttttaaggac     120 tacatagtta tctctatctt ctgtttcatg gtagcattcg gtggtttcgt ttttggtttc     180
gatacaggta ccataagtgg tttcgttaac atgtctgatt tcaaagacag attcggtcaa     240
catcacgctg atggtacacc ttacttgagt gacgttagag tcggtttgat gatctctatt     300
```

```
ttcaatgttg gttgtgccgt cggtggtatt ttcttgtgca agtagctga tgtttggggt      360
agaagaatag gtttgatgtt ctctatggct gtttacgttg tcggtatcat catccaaatc      420
tcttcatcca ccaagtggta ccaattttc atcggtagat taattgccgg tttagctgtc      480
ggtactgtaa gtgtagtttc tccattgttt atatcagaag tttcccctaa acaaatcaga      540
ggtacattgg tctgttgctt ccaattgtgt ataaccttgg gtatcttctt aggttattgc      600
actacatacg gtactaagac atataccgat tctagacaat ggagaatccc attgggttta      660
tgttttgcat gggccatatt gttagtcgta ggcatgttga atatgccaga tcacctaga       720
tatttggttg aaaagcatag aatcgatgaa gcaaagagaa gtatagccag atctaacaaa      780
atcccagaag aagacccttt cgtatacaca gaagttcaat tgatacaagc aggtatagaa      840
agagaagctt tggcaggtca agcctcatgg aaggaattga taacaggtaa acctaagatt      900
tttagaagag ttataatggg tatcatgttg caatctttgc aacaattgac tggtgacaac      960
tatttctttt attacggtac cactatattt caagctgtcg gtttgaaaga ctcattccaa     1020
acctccatca tcttgggtat cgttaacttc gcatcaactt tcgtcggtat ctatgtaatc     1080
gaaagattgg gtagaagatt atgtttgttg acaggtagtg ctgcaatgtt catatgcttc     1140
atcatctatt ctttgatagg tacccaacat ttgtacaagc aaggttacag taacgaaact     1200
tctaacacat acaaggcatc tggtaacgcc atgatcttta ttacttgttt gtacattttc     1260
tttttcgctt ccacatgggc aggtggtgtt tattgcataa tcagtgaatc ttacccatta     1320
agaatcagat caaaggccat gtccattgct actgccgcta actggttgtg gggtttctta     1380
atctcattct ttaccccttt tatcacttcc gctattcact tctattacgg ttttgttttc     1440
actggttgtt tggcattttc tttctttat gtttacttct tgtctacga aacaaagggt      1500
ttgtcattgg aagaagtcga tgaaatgtac gcttccggtg tattgccatt aaagtcagca     1560
tcctgggttc cacctaattt ggaacacatg gctcactccg ctggttacgc tggtgctgat     1620
aaggcaactg atgaacaagt ctga                                             1644
```

<210> SEQ ID NO 19
<211> LENGTH: 724
<212> TYPE: PRT
<213> ORGANISM: Thermoascus aurantiacus

<400> SEQUENCE: 19

```
Ala Cys Pro Tyr Met Thr Gly Glu Leu Pro Arg Ser Phe Ala Glu Asn
1               5                   10                  15

Pro His Ala Ile Asn Arg Arg Ala Glu Gly Gly Gly Ala Ala Ala
            20                  25                  30

Glu Thr Glu Lys Phe Leu Ser Gln Phe Tyr Leu Asn Asp Asn Asp Thr
        35                  40                  45

Phe Met Thr Thr Asp Val Gly Gly Pro Ile Glu Asp Gln Asn Ser Leu
    50                  55                  60

Ser Ala Gly Asp Arg Gly Pro Thr Leu Leu Glu Asp Phe Ile Leu Arg
65                  70                  75                  80

Gln Lys Ile Gln Arg Phe Asp His Glu Arg Val Pro Glu Arg Ala Val
                85                  90                  95

His Ala Arg Gly Ala Gly Ala His Gly Val Phe Thr Ser Tyr Ala Asp
            100                 105                 110

Trp Ser Asn Ile Thr Ala Ala Ser Phe Leu Ser Ala Ala Gly Lys Glu
        115                 120                 125

Thr Pro Val Phe Val Arg Phe Ser Thr Val Ala Gly Ser Arg Gly Ser
```

```
                130                 135                 140
Ala Asp Thr Ala Arg Asp Val His Gly Phe Ala Thr Arg Phe Tyr Thr
145                 150                 155                 160

Asp Glu Gly Asn Phe Asp Ile Val Gly Asn Asn Ile Pro Val Phe Phe
                165                 170                 175

Ile Gln Asp Ala Ile Gln Phe Pro Asp Leu Ile His Ala Val Lys Pro
            180                 185                 190

Ser Pro Asn Asn Glu Ile Pro Gln Ala Ala Thr Ala His Asp Ser Ala
            195                 200                 205

Trp Asp Phe Phe Ser Gln Gln Pro Ser Ser Leu His Thr Leu Phe Trp
        210                 215                 220

Ala Met Ala Gly His Gly Ile Pro Arg Ser Tyr Arg Asn Met Asp Gly
225                 230                 235                 240

Phe Gly Ile His Thr Phe Arg Phe Val Thr Asp Gly Ala Ser Lys
                245                 250                 255

Leu Val Lys Phe His Trp Thr Ser Leu Gln Gly Lys Ala Ser Leu Val
                260                 265                 270

Trp Glu Glu Ala Gln Ala Val Ala Gly Lys Asn Ala Asp Tyr His Arg
        275                 280                 285

Gln Asp Leu Trp Asp Ala Ile Glu Ala Gly Arg Tyr Pro Glu Trp Glu
        290                 295                 300

Leu Gly Val Gln Ile Met Asp Glu Glu Asp Gln Leu Arg Phe Gly Phe
305                 310                 315                 320

Asp Leu Leu Asp Pro Thr Lys Ile Val Pro Glu Glu Tyr Val Pro Ile
                325                 330                 335

Thr Lys Leu Gly Lys Met Gln Leu Asn Arg Asn Pro Leu Asn Tyr Phe
                340                 345                 350

Ala Glu Thr Glu Gln Ile Met Phe Gln Pro Gly His Val Val Arg Gly
            355                 360                 365

Ile Asp Phe Thr Glu Asp Pro Leu Leu Gln Gly Arg Leu Phe Ser Tyr
        370                 375                 380

Leu Asp Thr Gln Leu Asn Arg His Gly Gly Pro Asn Phe Glu Gln Ile
385                 390                 395                 400

Pro Ile Asn Arg Pro Arg Thr Pro Ile His Asn Asn Arg Asp Gly
                405                 410                 415

Ala Ala Gln Met Tyr Ile Pro Leu Asn Lys Ala Ala Tyr Thr Pro Asn
            420                 425                 430

Thr Leu Asn Asn Gly Ser Pro Lys Gln Ala Asn Gln Thr Val Gly Lys
        435                 440                 445

Gly Phe Phe Thr Thr Pro Gly Arg Thr Ala Ser Gly Arg Leu Val Arg
    450                 455                 460

Ala Val Ser Ser Thr Phe Ala Asp Val Trp Ser Gln Pro Arg Leu Phe
465                 470                 475                 480

Tyr Asn Ser Leu Val Pro Ala Glu Gln Gln Phe Leu Ile Asn Ala Ile
                485                 490                 495

Arg Phe Glu Thr Ala His Ile Thr Ser Asp Val Val Lys Asn Asn Val
            500                 505                 510

Ile Ile Gln Leu Asn Arg Val Ser Asn Leu Ala Lys Arg Val Ala
        515                 520                 525

Arg Ala Ile Gly Val Ala Glu Pro Glu Pro Asp Pro Thr Leu Tyr His
    530                 535                 540

Asn Asn Lys Thr Ala Asn Val Gly Val Phe Gly Lys Pro Leu Ala Arg
545                 550                 555                 560
```

```
Leu Asp Gly Leu Gln Val Gly Val Leu Ala Thr Val Asn Lys Pro Asp
            565                 570                 575

Ser Ile Lys Gln Ala Ala Ser Leu Lys Ala Ser Phe Ala Ala Asp Asn
        580                 585                 590

Val Asp Val Lys Val Ala Glu Arg Leu Ala Asp Gly Val Asp Glu
        595                 600                 605

Thr Tyr Ser Ala Ala Asp Ala Val Asn Phe Asp Ala Ile Leu Val Ala
        610                 615                 620

Asn Gly Ala Glu Gly Leu Phe Ala Arg Asp Ser Phe Thr Ala Arg Pro
625                 630                 635                 640

Ala Asn Ser Thr Thr Ala Thr Leu Tyr Pro Ala Gly Arg Pro Leu Gln
            645                 650                 655

Ile Leu Val Asp Gly Phe Arg Tyr Gly Lys Pro Val Gly Ala Leu Gly
            660                 665                 670

Ser Gly Ala Lys Ala Leu Asp Ala Ala Glu Ile Ser Thr Thr Arg Ala
            675                 680                 685

Gly Val Tyr Val Ala Asn Ser Thr Thr Asp Ser Phe Ile Asn Gly Val
            690                 695                 700

Arg Asp Gly Leu Arg Thr Phe Lys Phe Leu Asp Arg Phe Ala Ile Asp
705                 710                 715                 720

Glu Asp Ala Glu

<210> SEQ ID NO 20
<211> LENGTH: 1320
<212> TYPE: DNA
<213> ORGANISM: Bovine

<400> SEQUENCE: 20
atggcaaaag aatatttcc gtttactggt aaaattcctt tcgagggaaa ggatagtaaa        60
aatgtaatgg ctttccatta ttacgagccc gagaaagtcg tgatgggaaa gaagatgaag       120
gactggctga agttcgcaat ggcctggtgg cacacactgg gaggcgcttc tgcagaccag       180
ttcggtggtc aaactcgcag ctatgagtgg acaaggctg aatgcccgt acagcgtgca        240 aaggataaga tggacgctgg tttcgagatc atggataagc tgggtatcga gtacttctgc       300
ttccacgatg tagacctcgt tgaggaggct cccaccatcg ctgagtacga ggagcgcatg       360
aaggccatca ccgactacgc tcaggagaag atgaagcagt tccccaatat caagctgctc       420
tggggtaccg caaacgtatt cggcaacaag cgttatgcca atggcgcttc taccaacccc       480
gatttcgatg tggttgctcg tgcgattgtt cagatcaaga actctatcga cgctaccatc       540
aagcttggtg gtaccaacta tgtgttctgg ggtggtcgtg agggctacat gagcctgttg       600
aacaccgacc agaagcgtga aggagcac atggctacga tgctgggtat ggctcgtgac        660
tatgctcgcg ctaagggatt caagggtacg ttcctgattg agccgaagcc gatggagcct       720
tcaaagcacc agtatgatgt ggacacagag accgtgattg gcttcctgaa ggcacatggt       780
ctggataagg acttcaaggt gaacatcgag gtgaaccacg ctacattggc tggtcacacc       840
ttcgagcacg aactggcttg tgctgttgac gctggtatgc tgggttctat cgacgctaac       900
cgcggtgatg cccagaacgg ctgggatacc gaccagttcc ccatcgacaa ctttgagctg       960
acacaggcta tgctggagat catccgcaac ggtggtctgg gcaatggcgg taccaatttc      1020
gacgccaaga tccgtcgtaa ttctaccgac ctcgaggatc tcttcatcgc tcatatcagc      1080
ggtatggatg ccatggcccg cgccctgatg aatgcagccg atattcttga gaactctgaa      1140
```

```
ctgcccgcaa tgaagaaggc tcgctacgca agcttcgaca gcggtatcgg taaggacttc    1200
gaggatggca agctgacctt cgagcaggtt tacgagtatg gtaagaaggt tgaagagccg    1260
aagcagacct ctggcaagca ggagaagtac gagacaatcg tcgccctcca ctgcaaataa    1320
```

<210> SEQ ID NO 21
<211> LENGTH: 437
<212> TYPE: PRT
<213> ORGANISM: Trichoderma reesei
<220> FEATURE:
<221> NAME/KEY: mat_peptide
<222> LOCATION: (1)..(437)

<400> SEQUENCE: 21

Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
                20                  25                  30

Val Leu Asp Trp Asn Tyr Arg Trp Met His Asp Ala Asn Tyr Asn Ser
            35                  40                  45

Cys Thr Val Asn Gly Gly Val Asn Thr Thr Leu Cys Pro Asp Glu Ala
        50                  55                  60

Thr Cys Gly Lys Asn Cys Phe Ile Glu Gly Val Asp Tyr Ala Ala Ser
65                  70                  75                  80

Gly Val Thr Thr Ser Gly Ser Ser Leu Thr Met Asn Gln Tyr Met Pro
                85                  90                  95

Ser Ser Ser Gly Gly Tyr Ser Ser Val Ser Pro Arg Leu Tyr Leu Leu
                100                 105                 110

Asp Ser Asp Gly Glu Tyr Val Met Leu Lys Leu Asn Gly Gln Glu Leu
            115                 120                 125

Ser Phe Asp Val Asp Leu Ser Ala Leu Pro Cys Gly Glu Asn Gly Ser
        130                 135                 140

Leu Tyr Leu Ser Gln Met Asp Glu Asn Gly Gly Ala Asn Gln Tyr Asn
145                 150                 155                 160

Thr Ala Gly Ala Asn Tyr Gly Ser Gly Tyr Cys Asp Ala Gln Cys Pro
                165                 170                 175

Val Gln Thr Trp Arg Asn Gly Thr Leu Asn Thr Ser His Gln Gly Phe
            180                 185                 190

Cys Cys Asn Glu Met Asp Ile Leu Glu Gly Asn Ser Arg Ala Asn Ala
        195                 200                 205

Leu Thr Pro His Ser Cys Thr Ala Thr Ala Cys Asp Ser Ala Gly Cys
210                 215                 220

Gly Phe Asn Pro Tyr Gly Ser Gly Tyr Lys Ser Tyr Tyr Gly Pro Gly
225                 230                 235                 240

Asp Thr Val Asp Thr Ser Lys Thr Phe Thr Ile Ile Thr Gln Phe Asn
                245                 250                 255

Thr Asp Asn Gly Ser Pro Ser Gly Asn Leu Val Ser Ile Thr Arg Lys
            260                 265                 270

Tyr Gln Gln Asn Gly Val Asp Ile Pro Ser Ala Gln Pro Gly Gly Asp
        275                 280                 285

Thr Ile Ser Ser Cys Pro Ser Ala Ser Ala Tyr Gly Gly Leu Ala Thr
        290                 295                 300

Met Gly Lys Ala Leu Ser Ser Gly Met Val Leu Val Phe Ser Ile Trp
305                 310                 315                 320

Asn Asp Asn Ser Gln Tyr Met Asn Trp Leu Asp Ser Gly Asn Ala Gly
                325                 330                 335

```
Pro Cys Ser Ser Thr Glu Gly Asn Pro Ser Asn Ile Leu Ala Asn Asn
                340                 345                 350

Pro Asn Thr His Val Val Phe Ser Asn Ile Arg Trp Gly Asp Ile Gly
            355                 360                 365

Ser Thr Thr Asn Ser Thr Ala Pro Pro Pro Pro Ala Ser Ser Thr
    370                 375                 380

Thr Phe Ser Thr Thr Arg Arg Ser Ser Thr Thr Ser Ser Ser Pro Ser
385                 390                 395                 400

Cys Thr Gln Thr His Trp Gly Gln Cys Gly Gly Ile Gly Tyr Ser Gly
                405                 410                 415

Cys Lys Thr Cys Thr Ser Gly Thr Thr Cys Gln Tyr Ser Asn Asp Tyr
                420                 425                 430

Tyr Ser Gln Cys Leu
            435

<210> SEQ ID NO 22
<211> LENGTH: 397
<212> TYPE: PRT
<213> ORGANISM: Trichoderma reesei
<220> FEATURE:
<221> NAME/KEY: mat_peptide
<222> LOCATION: (1)..(397)

<400> SEQUENCE: 22

Gln Gln Thr Val Trp Gly Gln Cys Gly Gly Ile Gly Trp Ser Gly Pro
1               5                   10                  15

Thr Asn Cys Ala Pro Gly Ser Ala Cys Ser Thr Leu Asn Pro Tyr Tyr
                20                  25                  30

Ala Gln Cys Ile Pro Gly Ala Thr Thr Ile Thr Thr Ser Thr Arg Pro
            35                  40                  45

Pro Ser Gly Pro Thr Thr Thr Arg Ala Thr Ser Thr Ser Ser Ser
    50                  55                  60

Thr Pro Pro Thr Ser Ser Gly Val Arg Phe Ala Gly Val Asn Ile Ala
65                  70                  75                  80

Gly Phe Asp Phe Gly Cys Thr Thr Asp Gly Thr Cys Val Thr Ser Lys
                85                  90                  95

Val Tyr Pro Pro Leu Lys Asn Phe Thr Gly Ser Asn Asn Tyr Pro Asp
                100                 105                 110

Gly Ile Gly Gln Met Gln His Phe Val Asn Asp Gly Met Thr Ile
            115                 120                 125

Phe Arg Leu Pro Val Gly Trp Gln Tyr Leu Val Asn Asn Asn Leu Gly
130                 135                 140

Gly Asn Leu Asp Ser Thr Ser Ile Ser Lys Tyr Asp Gln Leu Val Gln
145                 150                 155                 160

Gly Cys Leu Ser Leu Gly Ala Tyr Cys Ile Val Asp Ile His Asn Tyr
                165                 170                 175

Ala Arg Trp Asn Gly Gly Ile Ile Gly Gln Gly Gly Pro Thr Asn Ala
            180                 185                 190

Gln Phe Thr Ser Leu Trp Ser Gln Leu Ala Ser Lys Tyr Ala Ser Gln
        195                 200                 205

Ser Arg Val Trp Phe Gly Ile Met Asn Glu Pro His Asp Val Asn Ile
    210                 215                 220

Asn Thr Trp Ala Ala Thr Val Gln Glu Val Val Thr Ala Ile Arg Asn
225                 230                 235                 240

Ala Gly Ala Thr Ser Gln Phe Ile Ser Leu Pro Gly Asn Asp Trp Gln
```

-continued

```
                245                 250                 255
Ser Ala Gly Ala Phe Ile Ser Asp Gly Ser Ala Ala Ala Leu Ser Gln
            260                 265                 270

Val Thr Asn Pro Asp Gly Ser Thr Thr Asn Leu Ile Phe Asp Val His
        275                 280                 285

Lys Tyr Leu Asp Ser Asp Asn Ser Gly Thr His Ala Glu Cys Thr Thr
    290                 295                 300

Asn Asn Ile Asp Gly Ala Phe Ser Pro Leu Ala Thr Trp Leu Arg Gln
305             310                 315                 320

Asn Asn Arg Gln Ala Ile Leu Thr Glu Thr Gly Gly Gly Asn Val Gln
            325                 330                 335

Ser Cys Ile Gln Asp Met Cys Gln Gln Ile Gln Tyr Leu Asn Gln Asn
            340                 345                 350

Ser Asp Val Tyr Leu Gly Tyr Val Gly Trp Gly Ala Gly Ser Phe Asp
        355                 360                 365

Ser Thr Tyr Val Leu Thr Glu Thr Pro Thr Gly Ser Gly Asn Ser Trp
    370                 375                 380

Thr Asp Thr Ser Leu Val Ser Ser Cys Leu Ala Arg Lys
385             390                 395
```

US 10,066,244 B2

PROCESS FOR PRODUCING ETHANOL AND FERMENTING ORGANISMS

CROSS-REFERENCE TO RELATED APPLICATIONS

This application is a 35 U.S.C. 371 national application of PCT/CN2015/090204 filed on Sep. 22, 2015, which claims priority or the benefit under 35 U.S.C. 119 of International Patent Application No. PCT/CN2014/087191 filed on Sep. 23, 2014, International Patent Application No. PCT/CN2014/093589 filed on Dec. 11, 2014, and International Patent Application No. PCT/CN2015/077496 filed on Apr. 27, 2015. The contents of these applications are fully incorporated herein by reference.

FIELD OF THE INVENTION

The present invention relates to improved processes for producing ethanol from cellulosic material and improved fermenting organisms.

BACKGROUND OF THE INVENTION

Ethanol is a transportation fuel commonly blending into gasoline. Cellulosic material is used as a feedstock in ethanol production processes. There are several processes in the art for making cellulose and hemicelluloses hydrolysates containing glucose, mannose, xylose and arabinose. Glucose and mannose are efficiently converted to ethanol during natural anaerobic metabolism. By far the most efficient ethanol producing microorganism is the yeast *Saccharomyces cerevisiae*. However, *Saccharomyces cerevisiae* lacks the necessary enzymes to convert the dominant sugar xylose into xylulose and is therefore unable to utilize xylose as a carbon source. To do so requires genetic engineering of *Saccharomyces cerevisiae* to express enzymes that can convert xylose into xylulose. One of the enzymes needed is xylose isomerase (E.C. 5.3.1.5) which converts xylose into xylulose, which can then be converted into ethanol during fermentation by *Saccharomyces cerevisiae*.

WO 2003/062430 discloses that the introduction of a functional *Piromyces* xylose isomerase (XI) into *Saccharomyces cerevisiae* allows slow metabolism of xylose via the endogenous xylulokinase (EC 2.7.1.17) encoded by XKS1 and the enzymes of the non-oxidative part of the pentose phosphate pathway and confers to the yeast transformants the ability to grow on xylose.

U.S. Pat. No. 8,586,336-B2 disclosed a *Saccharomyces cerevisiae* yeast strain expressing a xylose isomerase obtained by bovine rumen fluid. The yeast strain can be used to produce ethanol by culturing under anaerobic fermentation conditions.

Despite significant improvement of ethanol production processes from cellulosic material over the past decade there is still a desire and need for providing improved processes. To produce ethanol economically a fermentation organism that is biologically efficient is required.

SUMMARY OF THE INVENTION

The present invention also relates to processes of producing ethanol, comprising:
(a) saccharifying a cellulosic material with a cellulolytic enzyme composition;
(b) fermenting the saccharified cellulosic material with a fermenting microorganism to produce ethanol; wherein the fermenting organism is *Saccharomyces cerevisiae* CIBTS1260 (deposited under Accession No. NRRL Y-50973 at the Agricultural Research Service Culture Collection (NRRL), Illinois 61604 U.S.A.) or a fermenting organism strain having properties that are about the same as that of *Saccharomyces cerevisiae* CIBTS1260.

In a preferred embodiment the process comprises recovering the ethanol from the fermentation.

In an embodiment the yeast cell pitch is between 0.1 and 20 g DWC *Saccharomyces cerevisiae* CIBTS1260/L fermentation medium, such as 0.2-10 g/L, preferably 0.3-5 g/L, such as 0.4 g/L, such as around 1 g DWC/L or around 2 g DWC/L.

In another aspect the invention relates to recombinant fermenting organisms having properties that are the same as that of *Saccharomyces cerevisiae* CIBTS1260 (deposited under Accession No. NRRL Y-50973 at the Agricultural Research Service Culture Collection (NRRL), Illinois 61604 U.S.A.) or a fermenting organism having properties that are about the same as that of *Saccharomyces cerevisiae* CIBTS1260.

In a preferred embodiment the fermenting organism of the invention having properties that are about the same as that of *Saccharomyces cerevisiae* CIBTS1260 has one or more, such as all, of the following properties:
  higher xylose consumption compared to BSGX001 after 48 hours fermentation at 1 g DWC/L, 35° C., pH 5.5, in particular as described in Example 3;
  higher glucose consumption compared to BSGX001 after 48 hours fermentation at 1 g DWC/L, 35° C., pH 5.5, in particular as described in Example 3;
  higher ethanol production compared to BSGX001 after 48 hours fermentation at 1 g DWC/L, 35° C., pH 5.5, in particular as described in Example 3.

In an embodiment the fermenting organism of the invention comprises a gene encoding the amino acid sequence having xylose isomerase activity shown in SEQ ID NO: 2 in U.S. Pat. No. 8,586,336 B2 or SEQ ID NO: 13 herein, or an amino acid sequence being at least 80%, such as at least 85%, such as at least 90%, such as at least 95%, such as at least 96%, such as at least 97%, such as at least 98%, such as at least 99%, such as 100% identical to SEQ ID NO: 2 in U.S. Pat. No. 8,586,336 B2 or SEQ ID NO: 13 herein. The gene in the fermenting organism encoding the xylose isomerase may be the one shown in SEQ ID NO: 1 in U.S. Pat. No. 8,586,336-B2 (hereby incorporated by reference) or SEQ ID NO: 20 herein or a sequence having at least 80%, such as at least 85%, such as at least 90%, such as at least 95%, such as at least 96%, such as at least 97%, such as at least 98%, such as at least 99%, such as 100% identical thereto.

In an embodiment the fermenting organism of the invention has one or more, such as all, of the following genetic modifications:
  xylose isomerases gene (Ru-XI) obtained from bovine rumen fluid, in particular the one shown in SEQ ID NO: 20 herein, encoding the xylose isomerase shown in SEQ ID NO: 13 herein;
  optionally a pentose transporter gene (GXF1) from *Candida intermedia*, in particular the one shown in SEQ ID NO: 18;
  xylulokinase gene (XKS), in particular from a type strain of *Saccharomyces cerevisiae*;
  ribulose 5 phosphate 3-epimerase gene (RPE1), in particular from a type strain of *Saccharomyces cerevisiae*;
  ribulose 5 phosphate isomerase gene (RKI1), in particular from a type strain of *Saccharomyces cerevisiae*;

transketolase gene (TKL1) and transaldolase gene (TAL1), in particular from a type strain of *Saccharomyces cerevisiae*.

In a specific embodiment the fermenting organism is *Saccharomyces cerevisiae* CIBTS1260 (deposited under Accession No. NRRL Y-50973 at the Agricultural Research Service Culture Collection (NRRL), Illinois 61604 U.S.A.).

DETAILED DESCRIPTION OF THE INVENTION

Figure 1:
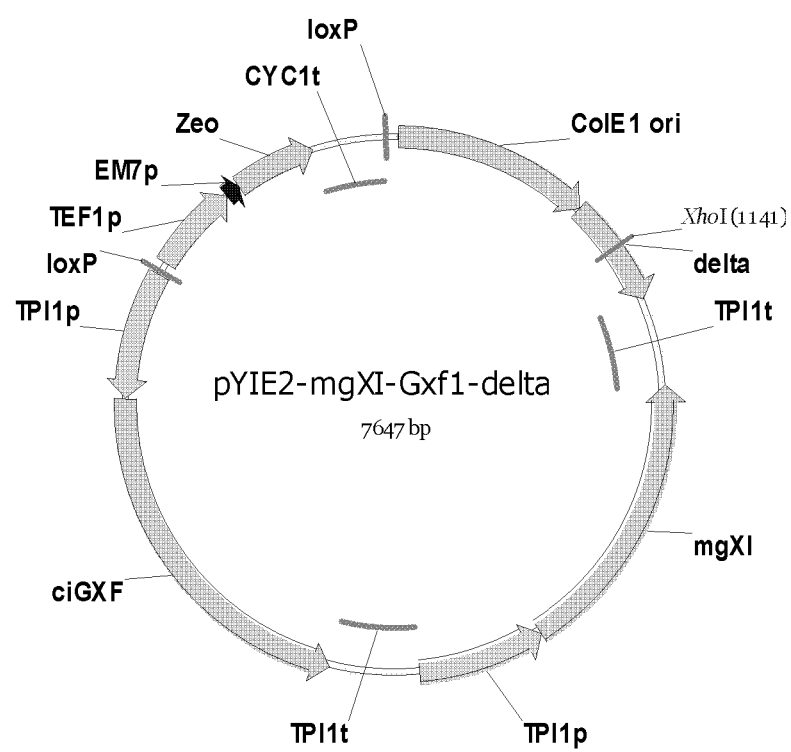
FIG. 1 shows a plasmid map of the plasmid pYIE2-mgXI-GXF1-delta harboring the mgXI and GXF expression cassettes.

The present invention provides improved processes for producing ethanol from lignocellulosic material using a fermenting organism.

Definitions

Auxiliary Activity 9: The term "Auxiliary Activity 9" or "AA9" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40 C-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST™ 1.5 L (Novozymes A/S, Bagsvrd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

Catalase: The term "catalase" means a hydrogen-peroxide:hydrogen-peroxide oxidoreductase (EC 1.11.1.6) that catalyzes the conversion of $2H_2O_2$ to $O_2+2H_2O$. For purposes of the present invention, catalase activity is determined according to U.S. Pat. No. 5,646,025. One unit of catalase activity equals the amount of enzyme that catalyzes the oxidation of 1 μmole of hydrogen peroxide under the assay conditions.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme composition or cellulase: The term "cellulolytic enzyme composition" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman N21 filter paper, microcrystalline cellulose, bacterial cellulose, algal cellulose, cotton, pretreated lignocellulose, etc. The most common total cellulolytic activity assay is the filter paper assay using Whatman N21 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is arundo, bagasse, bamboo, corn cob, corn fiber, corn stover, miscanthus, rice straw, switchgrass, or wheat straw.

In another embodiment, the cellulosic material is aspen, eucalyptus, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Endoglucanase: The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is cellulosic material.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrimann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylan degrading activity can be determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylose Isomerase: The term "Xylose Isomerase" or "XI" means an enzyme which can catalyze D-xylose into D-xylulose in vivo, and convert D-glucose into D-fructose in vitro. Xylose isomerase is also known as "glucose isomerase" and is classified as E.C. 5.3.1.5. As the structure of the enzyme is very stable, the xylose isomerase is one of the good models for studying the relationships between protein structure and functions (Karimaki et al., Protein Eng Des Sel, 12004, 17 (12):861-869). Moreover, the extremely important industrial application value makes the xylose isomerase is seen as important industrial enzyme as protease and amylase (Tian Shen et al., Microbiology Bulletin, 2007, 34 (2): 355-358; Bhosale et al., Microbiol Rev, 1996, 60 (2): 280-300). The scientists keep high concern and carried out extensive research on xylose isomerase. Since 1970s, the applications of the xylose isomerase have focused on the production of high fructose syrup and fuel ethanol. In recent years, scientists have found that under certain conditions, the xylose isomerase can be used for producing many important rare sugars, which are the production materials in the pharmaceutical industry, such as ribose, mannose, arabinose and lyxose (Karlmaki et al., Protein Eng Des Se, 12004, 17 (12): 861-869). These findings bring new vitality in the research on the xylose isomerase.

Processes of The Invention

The present invention also relates to processes of producing ethanol, comprising:
  (a) saccharifying a cellulosic material with a cellulolytic enzyme composition;
  (b) fermenting the saccharified cellulosic material with a fermenting microorganism to produce ethanol; wherein the fermenting organism is *Saccharomyces cerevisiae* CIBTS1260 (deposited under Accession No. NRRL Y-50973 at the Agricultural Research Service Culture Collection (NRRL), Illinois 61604 USA.) or a fermenting organism having properties that are about the same as that of *Saccharomyces cerevisiae* CIBTS1260.

In a preferred embodiment the process comprises recovering the ethanol from the fermentation medium.

The processing of the cellulosic material according to the present invention can be accomplished using methods conventional in the art. Moreover, the processes of the present invention can be implemented using any conventional biomass processing apparatus configured to operate in accordance with the invention.

Saccharification (i.e., hydrolysis) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF).

SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol Production and Utilization*, Wyman, C. E., ed., Taylor & Francis, Washington, D.C., 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation organismcan tolerate. It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment

In an embodiment the cellulosic material is pretreated before saccharification in step (a).

In practicing the processes of the present invention, any pretreatment process known in the art can be used to disrupt plant cell wall components of the cellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

In a preferred embodiment the cellulosic material is pretreated before saccharification (i.e., hydrolysis) and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment. The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, countercurrent reactors, or continuous counter-current shrinking bed reactors (Duff and Murray, 1996, *Bioresource Technol-* ogy 855: 1-33; Schell et al., 2004, *Bioresource Technology* 91: 179-188; Lee et al., 1999, *Adv. Biochem. Eng. Biotechnol.* 65: 93-115). In a specific embodiment the dilute acid pretreatment of cellulosic material is carried out using 4% w/w sulfuric acid at 180° C. for 5 minutes.

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt. %, e.g., 20-70 wt. % or 30-60 wt. %, such as around 40 wt. %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment. The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification

In the saccharification step (i.e., hydrolysis step), the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by a cellulolytic enzyme composition. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzymes(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 4.5 to about 5.5. The dry solids content is in the range of preferably about 5 to about 50 wt. %, e.g., about 10 to about 40 wt. % or about 20 to about 30 wt. %.

Saccharification in step (a) is carried out using a cellulolytic enzyme composition. Such enzyme compositions are described below in the "Cellulolytic Enzyme Composition"-section below. The cellulolytic enzyme compositions can comprise any protein useful in degrading the cellulosic material. In one aspect, the cellulolytic enzyme composition comprises or further comprises one or more (e.g., several) proteins selected from the group consisting of a cellulase, an AA9 (GH61) polypeptide, a hemicellulase, an esterase, an expansin, a ligninolytic enzyme, an oxidoreductase, a pectinase, a protease, and a swollenin.

In another aspect, the cellulase is preferably one or more (e.g., several) enzymes selected from the group consisting of an endoglucanase, a cellobiohydrolase, and a beta-glucosidase.

In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the oxidoreductase is preferably one or more (e.g., several) enzymes selected from the group consisting of a catalase, a laccase, and a peroxidase.

The enzymes or enzyme compositions used in a processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

In one aspect, an effective amount of cellulolytic or hemicellulolytic enzyme composition to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In one aspect, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO 2012/021401, and the soluble contents thereof. A liquor for cellulolytic enhancement of an AA9 polypeptide (GH61 polypeptide) can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

Fermentation

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

Fermenting Organism of The Invention

In this aspect the invention relates to recombinant fermenting organisms capable of converting hexoses and pentoses into ethanol.

In an embodiment the invention related to recombinant fermenting organisms having properties that are the same as that of *Saccharomyces cerevisiae* CIBTS1260 (deposited under Accession No. NRRL Y-50973 at the Agricultural Research Service Culture Collection (NRRL), Illinois 61604 U.S.A.) or a fermenting organism having properties that are about the same as that of *Saccharomyces cerevisiae* CIBTS1260.

In an embodiment the fermenting organism having properties that are about the same as that of *Saccharomyces cerevisiae* CIBTS1260 has one or more, such as all, of the following properties:

higher xylose consumption compared to BSGX001 after 48 hours fermentation at 1 g DWC/L, 35° C., pH 5.5, in particular as described in Example 3;
  higher glucose consumption compared to BSGX001 after 48 hours fermentation at 1 g DWC/L, 35° C., pH 5.5, in particular as described in Example 3;
  higher ethanol production compared to BSGX001 after 48 hours fermentation at 1 g DWC/L, 35° C., pH 5.5, in particular as described in Example 3.

In an embodiment the fermenting organism having properties that are about the same as that of *Saccharomyces cerevisiae* CIBTS1260 provides full xylose consumption by 48 hours fermentation under the process conditions in Example 3, i.e., 1 g DCW/L, 35° C., pH 5.5.

In an embodiment the fermenting organism having properties that are about the same as that of *Saccharomyces cerevisiae* CIBTS1260 provides full glucose consumption by 24 hours fermentation under the process conditions in Example 3, i.e., 1 g DCW/L, 35° C., pH 5.5.

In an embodiment the fermenting organism organism having properties that are about the same as that of *Saccharomyces cerevisiae* CIBTS1260 provides more than 30 g/L ethanol, such as more than 40 g/L ethanol, such as more than 45 g/L ethanol, such as approximately 47 g/L ethanol after 48 hours fermentation under the process conditions in Example 3, i.e., 1 g DCW/L, 35° C., pH 5.5.

In a preferred embodiment the recombinant fermenting organism is *Saccharomyces cerevisiae* CIBTS1260 (deposited under Accession No. NRRL Y-50973 at the Agricultural Research Service Culture Collection (NRRL), Illinois 61604 U.S.A.).

In an embodiment the fermenting organism of the invention comprises a gene encoding an amino acid sequence having xylose isomerase activity shown in SEQ ID NO: 2 in U.S. Pat. No. 8,586,336B2 or SEQ ID NO: 13 herein, or an amino acid sequence being at least 80%, such as at least 90%, such as at least 95%, such as at least 96%, such as at least 97%, such as at least 98%, such as at least 99%, such as 100% identical to SEQ ID NO: 2 in U.S. Pat. No. 8,586,336B2 or SEQ ID NO: 13 herein.

In an optional embodiment the fermenting organism of the invention comprises a pentose transporter gene, such as a GFX gene, in particular GFX1 from *Candida intermedia*, e.g., the sequence shown in SEQ ID NO: 18.

In an embodiment the pentose transporter gene comprised in the fermenting organism has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity SEQ ID NO: 18 herein.

In an embodiment the fermenting organism of the invention overexpresses a xylulokinase gene (XKS), in particular from a type strain of *Saccharomyces cerevisiae*.

In an embodiment the fermenting organism of the invention overexpresses a ribulose 5 phosphate 3-epimerase gene (RPE1), in particular from a type strain of *Saccharomyces cerevisiae*.

In an embodiment the fermenting organism of the invention overexpresses a ribulose 5 phosphate isomerase gene (RKI1), in particular from a type strain of *Saccharomyces cerevisiae*.

In an embodiment the fermenting organism of the invention overexpresses a transketolase gene (TKL1) and overexpresses a transaldolase gene (TAL1), in particular from a type strain of *Saccharomyces cerevisiae*.

In an embodiment the fermenting organism of the invention has one or more, such as one, two, three, four, five or all, of the following genetic modifications:

xylose isomerases gene (Ru-XI) obtained from bovine rumen fluid, in particular the one shown in SEQ ID NO: 20 herein, encoding the xylose isomerase shown in SEQ ID NO: 13 herein;
  optionally a pentose transporter gene (GXF1) from *Candida intermedia*, in particular the one shown in SEQ ID NO: 18;
  xylulokinase gene (XKS), in particular from a type strain of *Saccharomyces cerevisiae*;
  ribulose 5 phosphate 3-epimerase gene (RPE1), in particular from a type strain of *Saccharomyces cerevisiae*;
  ribulose 5 phosphate isomerase gene (RKI1), in particular from a type strain of *Saccharomyces cerevisiae*;
  transketolase gene (TKL1) and transaldolase gene (TAL1), in particular from a type strain of *Saccharomyces cerevisiae*.

For instance, in an embodiment the fermenting organism of the invention has the following genetic modifications:

xylose isomerases gene (Ru-XI) obtained from bovine rumen fluid, in particular the one shown in SEQ ID NO: 20 herein, encoding the xylose isomerase shown in SEQ ID NO: 13 herein;
  xylulokinase gene (XKS), in particular from a type strain of *Saccharomyces cerevisiae*;
  ribulose 5 phosphate 3-epimerase gene (RPE1), in particular from a type strain of *Saccharomyces cerevisiae*;
  ribulose 5 phosphate isomerase gene (RKI1), in particular from a type strain of *Saccharomyces cerevisiae*;
  transketolase gene (TKL1) and transaldolase gene (TAL1), in particular from a type strain of *Saccharomyces cerevisiae*.

Fermentation Stimulators

A fermentation stimulator can be used in a process of the invention described herein to further improve the fermentation, and in particular, the performance of the fermenting organism, such as, rate enhancement and product yield (e.g., ethanol yield). A "fermentation stimulator" refers to stimulators for growth of the fermenting organisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products

The fermentation product of the invention is ethanol.

Recovery

The fermentation product, i.e., ethanol, can optionally be recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Enzymes

Below sections describe polypeptides, enzymes and enzyme composition that may be used in processes of the invention.

Cellulolytic Enzyme Composition

According to the invention a cellulolytic enzyme composition is present or added during saccharification in step (a). A cellulolytic enzyme composition is an enzyme preparation containing one or more (e.g., several) enzymes that hydrolyze cellulosic material. Such enzymes include endoglucanase, cellobiohydrolase, beta-glucosidase, and/or combinations thereof.

The cellulolytic enzyme composition may be of any origin. In an embodiment the cellulolytic enzyme composition is derived from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*. In a preferred embodiment the cellulolytic enzyme preparation is derived from a strain of *Trichoderma reesei*.

The cellulolytic enzyme composition may further comprise one or more of the following polypeptides, such as enzymes: AA9 polypeptide (GH61 polypeptide) having cellulolytic enhancing activity, beta-glucosidase, xylanase, beta-xylosidase, CBH I, CBH II, or a mixture of two, three, four, five or six thereof.

The further polypeptide(s) (e.g., AA9 polypeptide) and/or enzyme(s) (e.g., beta-glucosidase, xylanase, beta-xylosidase, CBH I and/or CBH II may be foreign to the cellulolytic enzyme composition producing organism (e.g., *Trichoderma reesei*).

In an embodiment the cellulolytic enzyme preparation comprises an AA9 polypeptide having cellulolytic enhancing activity and a beta-glucosidase.

In another embodiment the cellulolytic enzyme preparation comprises an AA9 polypeptide having cellulolytic enhancing activity, a beta-glucosidase, and a CBH I.

In another embodiment the cellulolytic enzyme preparation comprises an AA9 polypeptide having cellulolytic enhancing activity, a beta-glucosidase, a CBH I and a CBH II.

Other enzymes, such as endoglucanases, may also be comprised in the cellulolytic enzyme composition.

As mentioned above the cellulolytic enzyme composition may comprise a number of difference polypeptides, including enzymes.

In an embodiment the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., WO 2005/074656), and *Aspergillus oryzae* beta-glucosidase fusion protein (e.g., one disclosed in WO 2008/057637, in particular shown as SEQ ID NOs: 59 and 60).

In another embodiment the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., SEQ ID NO: 2 in WO 2005/074656 or SEQ ID NO: 4 herein), and *Aspergillus fumigatus* beta-glucosidase (e.g., SEQ ID NO: 2 of WO 2005/047499 or SEQ ID NO: 5 herein).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO 2011/041397 or SEQ ID NO: 7 herein, and *Aspergillus fumigatus* beta-glucosidase (e.g., SEQ ID NO: 2 of WO 2005/047499 or SEQ ID NO: 5 herein).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO 2011/041397, and *Aspergillus fumigatus* beta-glucosidase (e.g., SEQ ID NO: 2 of WO 2005/047499 or SEQ ID NO: 5 herein) or a variant disclosed in WO 2012/044915 (hereby incorporated by reference), in particular one comprising one or more such as all of the following substitutions: F100D, S283G, N456E, F512Y.

In an embodiment the cellulolytic enzyme composition is a *Trichoderma reesei* cellulolytic composition, further comprising an AA9 (GH61A) polypeptide having cellulolytic enhancing activity, in particular the one derived from a strain of *Penicillium emersonii* (e.g., SEQ ID NO: 2 in WO 2011/041397 or SEQ ID NO: 7 herein), *Aspergillus fumigatus* beta-glucosidase (e.g., SEQ ID NO: 2 in WO 2005/047499 or SEQ ID NO: 5 herein) variant with one or more, in particular all of the following substitutions: F100D, S283G, N456E, F512Y and disclosed in WO 2012/044915; *Aspergillus fumigatus* Cel7A CBH1, e.g., the one disclosed as SEQ ID NO: 6 in WO2011/057140 and SEQ ID NO: 10 herein and *Aspergillus fumigatus* CBH II, e.g., the one disclosed as SEQ ID NO: 18 in WO 2011/057140 or SEQ ID NO: 11 herein.

In a preferred embodiment the cellulolytic enzyme composition is a *Trichoderma reesei*, cellulolytic enzyme composition, further comprising a hemicellulase or hemicellulolytic enzyme composition, such as an *Aspergillus fumigatus* xylanase (e.g. SEQ ID NO: 8 herein) and *Aspergillus fumigatus* beta-xylosidase (e.g. SEQ ID NO: 9 herein).

In an embodiment the cellulolytic enzyme composition also comprises a xylanase (e.g., derived from a strain of the genus *Aspergillus*, in particular *Aspergillus aculeatus* or *Aspergillus fumigatus*; or a strain of the genus *Talaromyces*, in particular *Talaromyces leycettanus*) and/or a beta-xylosidase (e.g., derived from *Aspergillus*, in particular *Aspergillus fumigatus*, or a strain of *Talaromyces*, in particular *Talaromyces emersonii*).

In an embodiment the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., WO 2005/074656 or SEQ ID NO: 4 herein), *Aspergillus oryzae* beta-glucosidase fusion protein (e.g., one disclosed in WO 2008/057637, in particular as SEQ ID NOs: 59 and 60), and *Aspergillus aculeatus* xylanase (e.g., XyI II in WO 94/21785 or SEQ ID NO: 6 herein).

In another embodiment the cellulolytic enzyme preparation comprises a *Trichoderma reesei* cellulolytic preparation, further comprising *Thermoascus aurantiacus* GH61A polypeptide having cellulolytic enhancing activity (e.g., SEQ ID NO: 2 in WO 2005/074656 or SEQ ID NO: 4 herein), *Aspergillus fumigatus* beta-glucosidase (e.g., SEQ ID NO: 2 of WO 2005/047499 or SEQ ID NO: 5 herein) and *Aspergillus aculeatus* xylanase (XyI II disclosed in WO 94/21785 or SEQ ID NO: 6 herein).

In another embodiment the cellulolytic enzyme composition comprises a *Trichoderma reesei* cellulolytic enzyme composition, further comprising *Thermoascus aurantiacus* AA9 (GH61A) polypeptide having cellulolytic enhancing activity (e.g., SEQ ID NO: 2 in WO 2005/074656 or SEQ ID NO: 4 herein), *Aspergillus fumigatus* beta-glucosidase (e.g., SEQ ID NO: 2 of WO 2005/047499 or SEQ ID NO: 5 herein) and *Aspergillus aculeatus* xylanase (e.g., XyI II disclosed in WO 94/21785 or SEQ ID NO: 6 herein).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO 2011/041397 or SEQ ID NO: 7 herein, *Aspergillus fumigatus* beta-glucosidase (e.g., SEQ ID NO: 2 of WO 2005/047499 or SEQ ID NO: 5 herein) and *Aspergillus fumigatus* xylanase (e.g., XyI III in WO 2006/078256 or SEQ ID NO: 8 herein).

In another embodiment the cellulolytic enzyme composition comprises a *Trichoderma reesei* cellulolytic enzyme composition, further comprising *Penicillium emersonii* AA9 (GH61A) polypeptide having cellulolytic enhancing activity, in particular the one disclosed in WO 2011/041397 or SEQ ID NO: 7 herein, *Aspergillus fumigatus* beta-glucosidase (e.g., SEQ ID NO: 2 of WO 2005/047499 or SEQ ID NO: 5 herein), *Aspergillus fumigatus* xylanase (e.g., XyI III in WO 2006/078256 or SEQ ID NO: 8 herein), and CBH I from *Aspergillus fumigatus*, in particular Cel7A CBH1 disclosed as SEQ ID NO: 2 in WO2011/057140 or SEQ ID NO: 10 herein.

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO 2011/041397 or SEQ ID NO: 7 herein, *Aspergillus fumigatus* beta-glucosidase (e.g., SEQ ID NO: 2 of WO 2005/047499 or SEQ ID NO: 5 herein), *Aspergillus fumigatus* xylanase (e.g., XyI III in WO 2006/078256 or SEQ ID NO: 8 herein), CBH I from *Aspergillus fumigatus*, in particular Cel7A CBH1 disclosed as SEQ ID NO: 2 in WO 2011/057140 or SEQ ID NO: 10 herein, and CBH II derived from *Aspergillus fumigatus* in particular the one disclosed as SEQ ID NO: 4 in WO 2013/028928 or SEQ ID NO: 11 herein.

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO 2011/041397 or SEQ ID NO: 7 herein, *Aspergillus fumigatus* beta-glucosidase (e.g., SEQ ID NO: 2 of WO 2005/047499 or SEQ ID NO: 5 herein) or variant thereof with one or more, in particular all, of the following substitutions: F100D, S283G, N456E, F512Y; *Aspergillus fumigatus* xylanase (e.g., XyI III in WO 2006/078256 or SEQ ID NO: 8 herein), CBH I from *Aspergillus fumigatus*, in particular Cel7A CBH I disclosed as SEQ ID NO: 2 in WO 2011/057140 or SEQ ID NO: 10 herein, and CBH II derived from *Aspergillus fumigatus*, in particular the one disclosed in WO 2013/028928 or SEQ ID NO: 11 herein.

In another embodiment the cellulolytic enzyme composition is a *Trichoderma reesei* cellulolytic enzyme composition comprising the CBH I of SEQ ID NO: 14 herein (GENSEQP Accession No. AZY49536 (WO2012/103293); a CBH II of SEQ ID NO:15 herein (GENSEQP Accession No. AZY49446 (WO2012/103288); a beta-glucosidase variant of SEQ ID NO: 5 herein (GENSEQP Accession No. AZU67153 (WO 2012/44915)), in particular with one or more, in particular all, of the following substitutions: F100D, S283G, N456E, F512Y; and AA9 (GH61 polypeptide) of SEQ ID NO: 7 herein (GENSEQP Accession No. BAL61510 (WO 2013/028912)).

In another embodiment the cellulolytic enzyme composition is a *Trichoderma reesei* cellulolytic enzyme composition comprising the CBH I of SEQ ID NO: 14 herein (GENSEQP Accession No. AZY49536 (WO2012/103293)); the CBH II of SEQ ID NO: 15 herein (GENSEQP Accession No. AZY49446 (WO2012/103288); the GH10 xylanase of SEQ ID NO: 16 herein (GENSEQP Accession No. BAK46118 (WO 2013/019827)); and the beta-xylosidase of SEQ ID NO: 17 herein (GENSEQP Accession No. AZI04896 (WO 2011/057140)).

In another embodiment the cellulolytic enzyme composition is a *Trichoderma reesei* cellulolytic enzyme composition comprising the CBH I of SEQ ID NO: 14 herein (GENSEQP Accession No. AZY49536 (WO2012/103293)); the CBH II of SEQ ID NO: 15 herein (GENSEQP Accession No. AZY49446 (WO2012/103288)); and the AA9 (GH61 polypeptide) of SEQ ID NO: 7 herein (GENSEQP Accession No. BAL61510 (WO 2013/028912)).

In another embodiment the cellulolytic enzyme composition is a *Trichoderma reesei* cellulolytic enzyme composition comprising the CBH I of SEQ ID NO: 14 herein (GENSEQP Accession No. AZY49536 (WO2012/103293)); the CBH II of SEQ ID NO: 15 herein (GENSEQP Accession No. AZY49446 (WO2012/103288)), the AA9 (GH61 polypeptide) of SEQ ID NO: 7 herein (GENSEQP Accession No. BAL61510 (WO 2013/028912)), and the catalase of SEQ ID NO: 19 herein (GENSEQP Accession No. BAC11005 (WO 2012/130120)).

In an embodiment the cellulolytic enzyme composition is a *Trichoderma reesei* cellulolytic enzyme composition comprising the CBH I of SEQ ID NO: 14 herein (GENSEQP Accession No. AZY49446 (WO2012/103288); the CBH II of SEQ ID NO: 15 herein (GENSEQP Accession No. AZY49446 (WO2012/103288)), the beta-glucosidase variant of SEQ ID NO: 5 herein (GENSEQP Accession No. AZU67153 (WO 2012/44915)), with one or more, in particular all, of the following substitutions: F100D, S283G, N456E, F512Y; the AA9 (GH61 polypeptide) of SEQ ID NO: 7 herein (GENSEQP Accession No. BAL61510 (WO 2013/028912)), the GH10 xylanase of SEQ ID NO: 16 herein (GENSEQP Accession No. BAK46118 (WO 2013/019827)), and the beta-xylosidase of SEQ ID NO: 17 herein (GENSEQP Accession No. AZI04896 (WO 2011/057140)).

In an embodiment the cellulolytic composition is a *Trichoderma reesei* cellulolytic enzyme preparation comprising EG I of SEQ ID NO: 21 herein (Swissprot Accession No. P07981), EG II of SEQ ID NO: 22 herein (EMBL Accession No. M19373), CBH I of SEQ ID NO: 14 herein; CBH II of SEQ ID NO: 15 herein; beta-glucosidase variant of SEQ ID NO: 5 herein with the following substitutions:

F100D, S283G, N456E, F512Y; the AA9 (GH61 polypeptide) of SEQ ID NO: 7 herein, GH10 xylanase of SEQ ID NO: 16 herein; and beta-xylosidase of SEQ ID NO: 17 herein.

All cellulolytic enzyme compositions disclosed in WO 2013/028928 are also contemplated and hereby incorporated by reference.

The cellulolytic enzyme composition comprises or may further comprise one or more (several) proteins selected from the group consisting of a cellulase, a AA9 (i.e., GH61) polypeptide having cellulolytic enhancing activity, a hemicellulase, an expansin, an esterase, a laccase, a ligninolytic enzyme, a pectinase, a peroxidase, a protease, and a swollenin.

In one embodiment the cellulolytic enzyme composition is a commercial cellulolytic enzyme composition. Examples of commercial cellulolytic enzyme compositions suitable for use in a process of the invention include: CELLIC® CTec (Novozymes A/S), CELLIC® CTec2 (Novozymes A/S), CELLIC® CTec3 (Novozymes A/S), CELLUCLAST™ (Novozymes A/S), SPEZYME™ CP (Genencor Int.), ACCELLERASE™ 1000, ACCELLERASE 1500, ACCELLERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme composition may be added in an amount effective from about 0.001 to about 5.0 wt. % of solids, e.g., about 0.025 to about 4.0 wt. % of solids or about 0.005 to about 2.0 wt. % of solids.

Endoglucanase

The cellulolytic enzyme composition used in a process of the invention may comprise an endoclucanase of any origin.

Examples of bacterial endoglucanases that can be used in the processes of the present invention, include, but are not limited to, Acidothermus cellulolyticus endoglucanase (WO 91/05039; WO 93/15186; U.S. Pat. No. 5,275,944; WO 96/02551; U.S. Pat. No. 5,536,655; WO 00/70031; WO 05/093050), Erwinia carotovara endoglucanase (Saarilahti et al., 1990, Gene 90: 9-14), Thermobifida fusca endoglucanase III (WO 05/093050), and Thermobifida fusca endoglucanase V (WO 05/093050).

Examples of fungal endoglucanases that can be used in the present invention, include, but are not limited to, Trichoderma reesei endoglucanase I (Penttila et al., 1986, Gene 45: 253-263, Trichoderma reesei Cel7B endoglucanase I (GenBank:M15665), Trichoderma reesei endoglucanase II (Saloheimo et al., 1988, Gene 63:11-22), Trichoderma reesei Cel5A endoglucanase II (GenBank: M19373), Trichoderma reesei endoglucanase III (Okada et al., 1988, Appl. Environ. Microbiol. 64: 555-563, GenBank: AB003694), Trichoderma reesei endoglucanase V (Saloheimo et al., 1994, Molecular Microbiology 13: 219-228, GenBank:Z33381), Aspergillus aculeatus endoglucanase (Ooi et al., 1990, Nucleic Acids Research 18: 5884), Aspergillus kawachii endoglucanase (Sakamoto et al., 1995, Current Genetics 27: 435-439), Fusarium oxysporum endoglucanase (GenBank:L29381), Humicola grisea var. thermoidea endoglucanase (GenBank:AB003107), Melanocarpus albomyces endoglucanase (GenBank:MAL515703), Neurospora crassa endoglucanase (GenBank:XM_324477), Humicola insolens endoglucanase V, Myceliophthora thermophila CBS 117.65 endoglucanase, Thermoascus aurantiacus endoglucanase I (GenBank:AF487830), Trichoderma reesei strain No. VTT-D-80133 endoglucanase (GenBank: M15665), Penicillium pinophilum endoglucanase (WO 2012/062220); and (WO 2013/019780).

In an embodiment the endoglucanase, such as one derived from Trichoderma reesei or homolog thereof, is selected from the group consisting of:
(i) an endoglucanase (EG) comprising the mature polypeptide of SEQ ID NO: 21 herein;
(ii) an endoglucanase (EG) an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 21 herein.

In an embodiment the endoglucanase, such as one derived from Trichoderma reesei or homolog thereof, is selected from the group consisting of:
(i) an endoglucanase (EG) comprising the mature polypeptide of SEQ ID NO: 22 herein;
(ii) an endoglucanase (EG) an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 22 herein.

AA9 (i.e., GH61) Polypeptide Having Cellulolytic Enhancing Activity

The cellulolytic enzyme composition used according to the invention may in one embodiment comprise one or more AA9 (GH61) polypeptides having cellulolytic enhancing activity. The cellulolytic enzyme composition used in a process of the invention may comprise an AA9 (GH61) polypeptide of any origin.

Examples of AA9 polypeptides useful in the processes of the present invention include, but are not limited to, AA9 polypeptides from Thielavia terrestris (WO 2005/074647, WO 2008/148131, and WO 2011/035027), Thermoascus aurantiacus (WO 2005/074656 and WO 2010/065830), Trichoderma reesei (WO 2007/089290 and WO 2012/149344), Myceliophthora thermophila (WO 2009/085935, WO 2009/085859, WO 2009/085864, WO 2009/085868, and WO 2009/033071), Aspergillus fumigatus (WO 2010/138754), Penicillium pinophilum (WO 2011/005867), Thermoascus sp. (WO 2011/039319), Penicillium sp. (emersoni0 (WO 2011/041397 and WO 2012/000892), Thermoascus crustaceous (WO 2011/041504), Aspergillus aculeatus (WO 2012/125925), Thermomyces lanuginosus (WO 2012/113340, WO 2012/129699, WO 2012/130964, and WO 2012/129699), Aurantiporus alborubescens (WO 2012/122477), Trichophaea saccata (WO 2012/122477), Penicillium thomii (WO 2012/122477), Talaromyces stipitatus (WO 2012/135659), Humicola insolens (WO 2012/146171), Malbranchea cinnamomea (WO 2012/101206), Talaromyces leycettanus (WO 2012/101206), and Chaetomium thermophilum (WO 2012/101206), and Talaromyces thermophilus (WO 2012/129697 and WO 2012/130950).

In one aspect, the AA9 polypeptide is used in the presence of a soluble activating divalent metal cation according to WO 2008/151043, e.g., manganese or copper.

In another aspect, the AA9 polypeptide is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

In one embodiment the cellulolytic enzyme composition comprises a AA9 (GH61) polypeptide having cellulolytic enhancing activity, such as one derived from the genus *Thermoascus*, such as a strain of *Thermoascus aurantiacus*, such as the one described in WO 2005/074656 as SEQ ID NO: 2 or SEQ ID NO: 4 herein; or one derived from the genus *Thielavia*, such as a strain of *Thielavia terrestris*, such as the one described in WO 2005/074647 as SEQ ID NO: 7 and SEQ ID NO: 8 and SEQ ID NO: 2 herein; or one derived from a strain of *Aspergillus*, such as a strain of *Aspergillus fumigatus*, such as the one described in WO 2010/138754 as SEQ ID NO: 2; or one derived from a strain derived from *Penicillium*, such as a strain of *Penicillium emersonii*, such as the one disclosed in WO 2011/041397 or SEQ ID NO: 7 herein.

In an embodiment the *Thermoascus aurantiacus* AA9 (GH61) polypeptide having cellulolytic enhancing activity or homolog thereof is selected from the group consisting of:
(i) a GH61 polypeptide having cellulolytic enhancing activity comprising the mature polypeptide of SEQ ID NO: 4 herein;
(ii) a GH61 polypeptide having cellulolytic enhancing activity comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 4 herein.

In another embodiment the Penicillium sp. AA9 (GH61) polypeptide having cellulolytic enhancing activity or homolog thereof is selected from the group consisting of:
(i) a GH61 polypeptide having cellulolytic enhancing activity comprising the mature polypeptide of SEQ ID NO: 7 herein;
(ii) a GH61 polypeptide having cellulolytic enhancing activity comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 7 herein.

Beta-Glucosidase

According to the invention a beta-glucosidase may be present and/or added in saccharification step (a). The cellulolytic enzyme composition used in a process of the invention may comprise a beta-glucosidase of any origin.

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 02/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may in one embodiment be one derived from a strain of the genus *Aspergillus*, such as *Aspergillus niger* or *Aspergillus oryzae*, such as the one disclosed in WO 2002/095014 or the fusion protein having beta-glucosidase activity disclosed in WO 2008/057637 as SEQ ID NOs: 59 and 60, or *Aspergillus fumigatus*, such as such as one disclosed in WO 2005/047499 or SEQ ID NO: 5 herein or an *Aspergillus fumigatus* beta-glucosidase variant, such as one disclosed in WO 2012/044915, such as one with the following substitutions: F100D, S283G, N456E, F512Y (using SEQ ID NO: 5 herein for numbering).

In another embodiment the beta-glucosidase is derived from a strain of the genus *Penicillium*, such as a strain of the *Penicillium brasilianum* disclosed in WO 2007/019442, or a strain of the genus *Trichoderma*, such as a strain of *Trichoderma reesei*.

In an embodiment beta-glucosidase is an *Aspergillus fumigatus* beta-glucosidase or homolog thereof selected from the group consisting of:
(i) a beta-glucosidase comprising the mature polypeptide of SEQ ID NO: 5 herein;
(ii) a beta-glucosidase comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 5 herein.

In an embodiment the beta-glucosidase is a variant comprises a substitution at one or more (several) positions corresponding to positions 100, 283, 456, and 512 of the mature polypeptide of SEQ ID NO: 5 herein, wherein the variant has beta-glucosidase activity.

In an embodiment the beta-glucosidase is a variant of (a) a polypeptide comprising the mature polypeptide of SEQ ID NO: 5 herein; (b) a polypeptide having at least 80% sequence identity to the mature polypeptide of SEQ ID NO: 5 herein or (c) a fragment of the mature polypeptide of SEQ ID NO: 5 herein, which has beta-glucosidase activity.

In an embodiment the beta-glucosidase variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 5 herein.

In an embodiment the beta-glucosidase is from a strain of *Aspergillus*, such as a strain of *Aspergillus fumigatus*, such as *Aspergillus fumigatus* beta-glucosidase (e.g., shown in SEQ ID NO: 5 herein), which comprises one or more substitutions selected from the group consisting of L89M, G91L, F100D, I140V, I186V, S283G, N456E, and F512Y; such as a variant thereof with the following substitutions:
F100D+S283G+N456E+F512Y;
L89M+G91L+I186V+I140V;
I186V+L89M+G91L+I140V+F100D+S283G+N456E+F512Y.

In an embodiment the number of substitutions is between 1 and 10, such 1 and 8, such as 1 and 6, such as 1 and 4, such as 1, 2, 3, 4, 5, 6, 7, 8, 9 or 10 substitutions.

In an embodiment the variant comprises a substitution at a position corresponding to position 100, a substitution at a position corresponding to position 283, a substitution at a position corresponding to position 456, and/or a substitution at a position corresponding to position 512.

In a preferred embodiment the beta-glucosidase variant comprises the following substitutions: Phe100Asp, Ser283Gly, Asn456Glu, Phe512Tyr in SEQ ID NO: 5 herein.

Cellobiohydrolase

The cellulolytic enzyme composition used in a process of the invention may comprise a cellobiohydrolase, such as CBH I and/or CBH II, of any origin.

Examples of cellobiohydrolases useful in the present invention include, but are not limited to, *Aspergillus aculeatus* cellobiohydrolase II (WO 2011/059740), *Aspergillus fumigatus* cellobiohydrolase I (WO 2013/028928), *Aspergillus fumigatus* cellobiohydrolase II (WO 2013/028928), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Penicillium occitanis* cellobiohydrolase I (GenBank:AY690482), *Talaromyces emersonii* cellobiohydrolase I (GenBank:AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086). Cellobiohydrolase I.

Cellobiohydrolase I

The cellulolytic enzyme composition used in a process of the invention may in one embodiment comprise one or more CBH I (cellobiohydrolase I). In one embodiment the cellulolytic enzyme composition comprises a cellobiohydrolase I (CBH I), such as one derived from a strain of the genus *Aspergillus*, such as a strain of *Aspergillus fumigatus*, such as the Cel7A CBH I disclosed in SEQ ID NO: 6 in WO 2011/057140 or SEQ ID NO: 10 herein; a strain of the genus *Trichoderma*, such as a strain of *Trichoderma reesei*; or a strain of the genus *Talaromyces*, such as a strain of *Talaromyces leycettanus*. preferably the one shown in SEQ ID NO: 14 herein or GENSEQP Accession No. AZY49536 (WO2012/103293).

In an embodiment the *Aspergillus fumigatus* cellobiohydrolase I or homolog thereof is selected from the group consisting of:
(i) a cellobiohydrolase I comprising the mature polypeptide of SEQ ID NO: 10 herein;
(ii) a cellobiohydrolase I comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 10 herein.

In another embodiment the cellobiohydrolase I, e.g., one derived from a strain of *Talaromyces leycettanus*, is selected from the group consisting of:
(i) a cellobiohydrolase I comprising the mature polypeptide of SEQ ID NO: 14 herein;
(ii) a cellobiohydrolase I comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 14 herein.

Cellobiohydrolase II

The cellulolytic enzyme composition used according to the invention may in one embodiment comprise one or more CBH II (cellobiohydrolase II). In one embodiment the cellobiohydrolase II (CBHII), such as one derived from a strain of the genus *Aspergillus*, such as a strain of *Aspergillus fumigatus*, such as the one in SEQ ID NO: 11 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*; or a strain of the genus *Talaromyces*, such as a strain of *Talaromyces leycettanus*, preferably the one shown in SEQ ID NO: 15 herein or GENSEQP Accession No. AZY49446 (WO2012/103288).

In an embodiment the *Aspergillus fumigatus* cellobiohydrolase II or homolog thereof is selected from the group consisting of:
(i) a cellobiohydrolase II comprising the mature polypeptide of SEQ ID NO: 11 herein;
(ii) a cellobiohydrolase II comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 11 herein.

In another embodiment the cellobiohydrolase II, e.g., one derived from a strain of *Talaromyces leycettanus*, is selected from the group consisting of:
(i) a cellobiohydrolase II comprising the mature polypeptide of SEQ ID NO: 15 herein;
(ii) a cellobiohydrolase II comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 15 herein.

Hemicellulases

According to the invention a hemicellulase may be present and/or added during saccharification in step (a). The hemicellulase may be in the form of a hemicellulolytic enzyme composition. The hemicellulase may be of any origin, but preferably of fungal or bacterial origin.

The term "hemicellulase" or "hemicellulolytic enzyme" means one or more (several) enzymes that hydrolyze a hemicellulosic material. See, for example, Shallom and Shoham, 2003, Microbial hemicellulases. *Current Opinion In Microbiology*, 6(3): 219-228. Hemicellulases are key components in the degradation of plant biomass. Examples of hemicellulases include, but are not limited to, an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families marked by numbers. Some families, with overall similar fold, can be further grouped into clans, marked alphabetically (e.g., GH-A). A most informative and updated classification of these and other carbohydrate active enzymes is available on the Carbohydrate-Active Enzymes (CAZy) database. Hemicellulolytic enzyme activities can be measured according to Ghose and Bisaria, 1987, *Pure & Appl. Chem.* 59: 1739-1752.

In an embodiment the hemicellulase present and/or added in saccharification is a hemicellulolytic enzyme composition. In an embodiment the hemicellulolytic enzyme composition is cellulolytic enzyme composition from *Trichoderma reesei*, further comprising a xylanase and/or a beta-xylosidase. In a preferred embodiment the hemicellulolytic enzyme composition is a cellulolytic enzyme composition from *Trichoderma reesei*, further comprising *Aspergillus fumigatus* xylanase (XYL III shown in SEQ ID NO: 8 herein) and *Aspergillus fumigatus* beta-xylosidase (SEQ ID NO: 9 herein).

The hemicellulase or hemicellulolytic enzyme preparation may preferably be added in concentrations between 0.01 and 20 mg EP/g cellulose, such as 0.1-1 mg EP/g cellulose.

Xylanases

In a preferred embodiment the hemicellulase is a xylanase or the hemicellulolytic enzyme composition comprises a xylanase. The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thermomyces lanuginosus* (GeneSeqP: BAA22485), *Talaromyces thermophilus* (GeneSeqP: BAA22834), *Thielavia terrestris* NRRL 8126 (WO 2009/079210), and *Trichophaea saccata* (WO 2011/057083).

Examples of specifically contemplated xylanases include GH10 xylanases, such as one derived from a strain of the genus *Aspergillus*, such as a strain from *Aspergillus fumigatus*, such as the one disclosed as Xyl III in WO 2006/078256, or *Aspergillus aculeatus*, such as the one disclosed in WO 94/21785 as SEQ ID NO: 5 (Xyl II).

The xylanase may be comprised in a cellulolytic enzyme preparation which further includes a xylanase. In one embodiment hemicellulase is a cellulolytic enzyme preparation further comprising a xylanase, preferably a GH10 xylanase, such as one derived from a strain of the genus *Aspergillus*, such as a strain from *Aspergillus fumigatus*, such as the one disclosed as Xyl III in WO 2006/078256, or *Aspergillus aculeatus*, such as the one disclosed in WO 94/21785 as SEQ ID NO: 5 (Xyl II) or SEQ ID NO: 6 herein.

In an embodiment the xylanase is derived from *Aspergillus aculatues*, such as the one shown in SEQ ID NO: 6 herein. In a preferred embodiment the xylanase is derived from *Aspergillus fuminatus*, such as the one shown in SEQ ID NO: 8 herein.

Contemplated xylanases also include those comprising an amino acid sequence having at least 60%, at least 70%, at least 80%, at least 85%, at least 90%, at least 95% identity, at least 97%, at least 98%, at least 99% identity to the *Aspergillus fumigatus* xylanase in WO 2006/078256 shown as SEQ ID NO: 8 herein, or the *Aspergillus aculeatus* xylanase disclosed in WO 94/21785 as SEQ ID NO: 5 (Xyl II) or SEQ ID NO: 6 herein.

In an embodiment the xylanase, e.g., derived from a strain of *Talaromyces leycettanus*, comprised in the cellulolytic enzyme composition, has an amino acid sequence having at least 60%, at least 70%, at least 80%, at least 85%, at least 90%, at least 95% identity, at least 97%, at least 98%, at least 99% identity to SEQ ID NO: 16 herein.

Beta-Xylosidases

In a preferred embodiment the hemicellulase used in a process of the invention is a beta-xylosidase, or the hemicellulolytic enzyme composition comprises a beta-xylosidase. The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

Examples of beta-xylosidases useful in the processes of the present invention include, but are not limited to, beta-xylosidases from *Neurospora crassa* (SwissProt:Q7SOW4), *Trichoderma reesei* (UniProtKB/TrEMBL:Q92458), *Talaromyces emersonii* (Swiss Prot:Q8X212), and *Talaromyces thermophilus* (GeneSeqP:BAA22816).

Examples of specifically contemplated beta-xylosidase includes the one derived from a strain of the genus *Aspergillus*, such as a strain of *Aspergillus fumigatus*, such as the one disclosed in WO 2013/028928 (Example 16 and 17) or SEQ ID NO: 9 herein, or derived from a strain of *Trichoderma*, such as a strain of *Trichoderma reesei*, such as the mature polypeptide of SEQ ID NO: 58 in WO 2011/057140 or SEQ ID NO: 1 herein.

The beta-xylosidase used in a process of the invention may be comprised in a cellulolytic enzyme composition. In one embodiment the hemicellulase is a cellulolytic enzyme composition; such as *Trichoderma reesei* cellulolytic enzyme composition; further comprising a beta-xylosidase, such as one derived from a strain of the genus *Aspergillus*, such as a strain of *Aspergillus fumigatus* (e.g., one disclosed in WO 2011/057140 or SEQ ID NO: 9 herein), such as one disclosed in WO 2013/028928 (Examples 16 and 17), or derived from a strain of *Trichoderma*, such as a strain of *Trichoderma reesei*, such as the mature polypeptide of SEQ ID NO: 58 in WO 2011/057140.

Contemplated beta-xylosidases also include those comprising an amino acid sequence having at least 60%, at least 70% at least 80%, at least 85%, at least 90%, at least 95% identity, at least 97%, at least 98%, at least 99% identity to the *Aspergillus fumigatus* beta-xylosidase disclosed as SEQ ID NO: 206 in WO 2011/057140 or SEQ ID NO: 9 herein or any of the beta-xylosidases mentioned herein.

In an embodiment the beta-xylosidase, e.g., derived from a strain of *Talaromyces emersonii, comprised in the cellulolytic enzyme composition, has an amino acid sequence having at least* 60%, at least 70%, at least 80%, at least 85%, at least 90%, at least 95% identity, at least 97%, at least 98%, at least 99% identity to SEQ ID NO: 17 herein.

The hemicellulase used in a process of the invention may comprise a commercial hemicellulase product. Examples of commercial hemicellulase products include, for example, SHEARZYME™ (Novozymes A/S), CELLIC™ HTec (Novozymes A/S), CELLIC™ HTec2 (Novozymes A/S), CELLIC™ HTec3 (Novozymes), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740 L. (Biocatalysts Limit, Wales, UK), and DEPOL™ 762P (Biocatalysts Limit, Wales, UK).

Catalases

The cellulolytic enzyme compositions may comprise a catalase. The catalase may be any catalase. The catalase may include, but is not limited to, an E.C. 1.11.1.6 or E.C. 1.11.1.21 catalase.

Examples of useful catalases include, but are not limited to, catalases from *Alcaligenes aquamarinus* (WO 98/00526), *Aspergillus lentilus, Aspergillus fumigatus, Aspergillus niger* (U.S. Pat. No. 5,360,901), *Aspergillus oryzae* (JP 2002223772A; U.S. Pat. No. 6,022,721), *Bacillus thermoglucosidasius* (JP 1 1243961A), *Humicola insolens* (WO 2009/104622, WO 2012/130120), *Malbranchea cinnamomea, Microscilla furvescens* (WO 98/00526), *Neurospora crassa, Penicillium emersonii* (WO 2012/130120), *Penicillium pinophilum, Rhizomucor pusillus, Saccharomyces pastorianus* (WO 2007/105350), *Scytalidium thermophilum, Talaromyces stipitatus* (WO 2012/130120), *Thermoascus aurantiacus* (WO 2012/130120), *Thermus brockianus* (WO 2005/044994), and *Thielavia terrestris* (WO 2010/074972).

Non-limiting examples of useful catalases are catalases from *Bacillus pseudofirmus* (UNI PROT:P30266), *Bacillus* subtilis (UNIPROT:P42234), *Humicola grisea* (GeneSeqP: AXQ55105), *Neosartorya fischeri* (UNIPROT:A1DJU9), *Penicillium emersonii* (GeneSeqP:BAC10987), *Penicillium pinophilum* (GeneSeqP:BAC10995), *Scytalidium thermophilum* (GeneSeqP:AAWO6109 or ADT89624), *Talaromyces stipitatus* (GeneSeqP:BAC10983 or BAC11039; UNIPROT:B8MT74), and *Thermoascus aurantiacus* (GeneSeqP:BAC11005). The accession numbers are incorporated herein in their entirety.

The cellulolytic enzyme compositions may in a preferred embodiment comprise a catalase, e.g., one derived from *Thermoascus*, in particular *Thermoascus aurantiacus*, in particular the one shown in WO 2012/130120 or SEQ ID NO: 19 herein.

In an embodiment the catalase, e.g., one derived from a strain of *Thermoascus auranticus*, is selected from the group consisting of:

(i) a catalase comprising the mature polypeptide of SEQ ID NO: 19 herein;

(ii) a catalase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 19 herein.

The protein content of the catalase is in the range of about 0.5% to about 10%, e.g., about 0.5% to about 7%, about 0.5% to about 5%, about 0.5% to about 4%, about 0.5% to about 3%, about 0.5% to about 2%, and about 0.5% to about 1% of total enzyme protein in the saccharification/hydrolysis reaction.

In an embodiment, the protein ratio of catalase to cellulolytic enzyme composition is in the range of about 1:200 to about 1:10, e.g., about 1:100 to about 1:15 or about 1:50 to about 1:25.

The present invention is further described by the following examples that should not be construed as limiting the scope of the invention.

Materials & Methods

Materials:

Cellulolytic Enzyme Composition CA ("CA"): Cellulolytic enzyme preparation derived from *Trichoderma reesei* further comprising GH61A polypeptide having cellulolytic enhancing activity derived from a strain of *Penicillium emersonii* (SEQ ID NO: 2 in WO 2011/041397 or SEQ ID NO: 7 herein), *Aspergillus fumigatus* beta-glucosidase (SEQ ID NO: 2 in WO 2005/047499 or SEQ ID NO: 5 herein) variant F100D, S283G, N456E, F512Y) disclosed in WO 2012/044915; *Aspergillus fumigatus* Cel7A CBH1 disclosed as SEQ ID NO: 6 in WO2011/057140 and SEQ ID NO: 10 herein and *Aspergillus fumigatus* CBH II disclosed as SEQ ID NO: 18 in WO 2011/057140 and SEQ ID NO: 11 herein. Further, Cellulolytic Enzyme Preparation CA further comprises 10% of a cellulolytic enzyme preparation from *Trichoderma reesei*, further comprising *Aspergillus fumigatus* xylanase (SEQ ID NO: 8 herein) and *Aspergillus fumigatus* beta-xylosidase (SEQ ID NO: 9 herein).

Cellulolytic Enzyme Composition CB ("CB"): *Trichoderma reesei* cellulolytic enzyme preparation comprising EG I of SEQ ID NO: 21 herein, EG II of SEQ ID NO: 22 herein, CBH I of SEQ ID NO: 14 herein; CBH II of SEQ ID NO: 15 herein; beta-glucosidase variant of SEQ ID NO: 5 herein with the following substitutions: F100D, S283G, N456E, F512Y; the AA9 (GH61 polypeptide) of SEQ ID NO: 7 herein, GH10 xylanase of SEQ ID NO: 16 herein; and beta-xylosidase of SEQ ID NO: 17 herein.

CIBTS1260: *Saccharomyces cerevisiae* yeast (deposited by Novozymes A/S under the terms of the Budapest Treaty with the Agricultural Research Service Culture Collection (NRRL), 1815 North University Street, Peoria, Ill. 61604 U.S.A.) and given the following accession number:

| Deposit | Accession Number | Date of Deposit |
|---|---|---|
| CIBTS1260 | NRRL Y-50973 | Sep. 5, 2014 |

BSGX001 is disclosed in U.S. Pat. No. 8,586,336-B2 (hereby incorporated by reference) and was constructed as follows: Host *Saccharomyces cerevisiae* strain BSPX042 (phenotype: ura3-251, overexpression of XKS1; overexpression of RPE1, RKI1, TAL1, and TKL1, which are genes in PPP; knockout of aldose reductase gene GRE3; and damage of electron transport respiratory chain by deleting gene COX4 after adaptive evolution), was transformed with vector pJFE3-RuXI inserted with xylose isomerase gene (SEQ ID NO: 1 in U.S. Pat. No. 8,586,336-B2 or SEQ ID NO: 20 herein) encoding the RuXI shown in SEQ ID NO: 2 in U.S. Pat. No. 8,586,336-B2 or SEQ ID NO: 13 herein.

Methods:

Identity

The relatedness between two amino acid sequences or between two polynucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two polynucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

EXAMPLES

Example 1

Construction of the Strain CIBTS1000

A diploid *Saccharomyces cerevisiae* strain that is known to be an efficient ethanol producer from glucose was identified. *S. cerevisiae* strain CCTCC M94055 from the Chinese Center for Type Culture Collection (CCTCC) was used.

A xylose isomerase termed mgXI was cloned from a meta genomics project meaning that the donor organism is not known. The isolation and the characteristics of this xylose isomerase are described in CN patent application No. 102174549A or US patent Publication No. 2012/0225452.

A pentose transporter termed GXF was cloned from *Candida intermedia* using standard methods. This xylose transporter was described by D. Runquist et. al. (Runquist D, Fonseca C, Radstrom P, Spencer-Martins I, Hahn-Hagerdal B: "Expression of the Gxf1 transporter from *Candida intermedia* improves fermentation performance in recombinant xylose-utilizing *Saccharomyces cerevisiae*". Appl Microbiol Biotechnol 2009, 82:123-130).

The xylose isomerase gene was fused to the Triose Phosphate Isomerase (TPI) promoter from *Saccharomyces cerevisiae* and the TPI terminator using standard methods so that the expression of the xylose isomerase in *S. cerevisiae* was controlled by the TPI expression signals.

The GXF gene was fused to the TPI expression signals in the same way.

These two expression cassettes were inserted into an *Escherichia coli* cloning vector containing:

The *E. coli* colE1 origin of replication securing that the plasmid could be propagated in *E. coli*.

A delta (δ) sequence fragment from *Saccharomyces cerevisiae*.

A Zeocin resistance marker from *Streptoalloteichus hindustanus* for selection of Zeocin resistant *E. coli* or *S. cerevisiae* transformants. A double promoter was fused to the 5' end of the Zeocin gene consisting of an *S. cerevisiae* Translation Elongation Factor (TEF1) promoter and an *E. coli* EM7 promoter. The *S. cerevisiae* CYC1 terminator was added to the 3' end of the Zeocin gene. The entire Zeocin expression cassette was flanked by loxP sites to enable deletion of this expression cassette by Cre-lox recombination (B. Sauer: "Functional expression of the Cre-Lox site specific recombination system in the yeast *Saccharomyces cerevisiae*." Mol. Cell. Biol. 1987, 7: 2087-2096).

The Xylose isomerase/pentose transporter expression plasmid was termed pYIE2-mgXI-GXF1-δ and is shown in FIG. 1.

The plasmid pYIE2-mgXI-GXF1-delta was first linierized by XhoI digestion and then transformed into the parental strain *Saccharomyces cerevisia* CCTCC M94055 following selection for zeocin resistant transformants. A strain termed CIBTS0912 was isolated having the plasmid integrated into a delta sequence. The zeocin resistance cassette located between the two loxP sites were then deleted by transient CRE recombinase expression resulting in the strain CIBTS0914.

Figure 2:
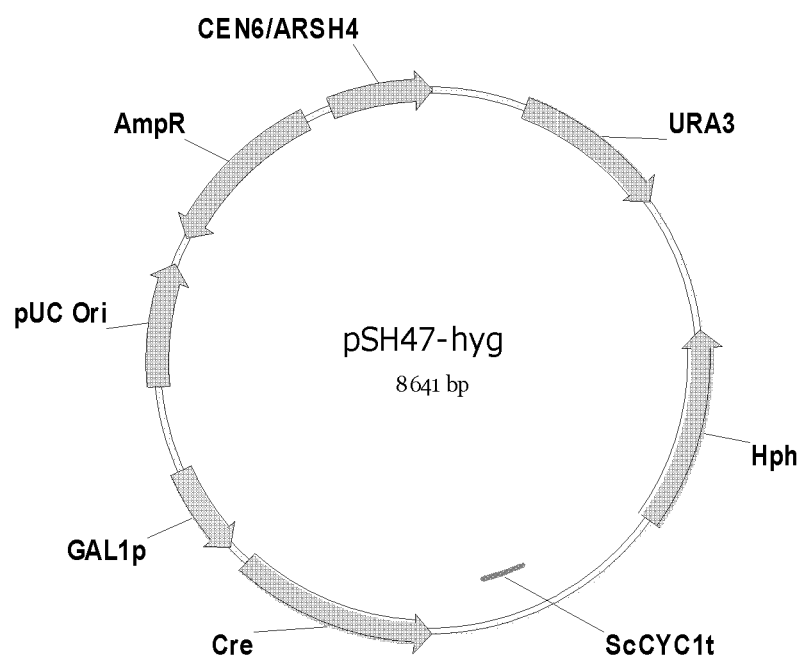
FIG. 2 shows a plasmid map of the plasmid used pSH47-hyg.

The transient CRE recombinase expression was achieved similar to the yeast standard method described by Prein et. al. (Prein B, Natter K, Kohlwein S D. "*A novel strategy for constructing N-terminal chromosomal fusions to green fluorescent protein in the yeast Saccharomyces cerevisiae*". FEBS Lett. 2000: 485, 29-34.) transforming with an unstable plasmid expressing the CRE recombinase followed by curing for that plasmid again. In this work the kanamycin gene of the yeast standard vector pSH47 was replaced with a hygromycin resistance marker so that rather than selecting for kanamycin resistance, selection for hygromycin was used. A plasmid map of the plasmid used pSH47-hyg is shown in FIG. 2.

| Gene/element name | Function | origin |
|---|---|---|
| Cre | Recombinase that catalyse recombination between lox sites | *Saccharomyces cerevisiae.* |
| GAL1p | Yeast promoter induced by galactose | *Saccharomyces cerevisiae.* |
| ScCYC1t | Yeast terminator | *Saccharomyces cerevisiae.* |
| hph | Hygromycin resistance gene. | *Streptomyces hygroscopicus.* |
| URA3 | Auxotrophic selection marker | *Saccharomyces cerevisiae.* |
| CEN6/ARSH4 | Replication origin | *Saccharomyces cerevisiae.* |
| pUC Ori | *E. coli* replication origin | *Escherichia coli* |
| AmpR | Ampicillin resistance gene | *Escherichia coli* |

The strain CIBTS0914 was transformed with XhoI digested pYIE2-mgXI-GXF1-δ again in order to increase the copy number of the two expression cassettes and a zeocin resistant strain, CIBTS0916 was selected.

In order to overexpress the genes of the pentose phosphate pathway, an expression plasmid harboring the selected pentose phosphate pathway genes was assembled.

The genes selected for overexpression were:

1. Xylulo kinase (XKS1).
2. Trans-aldolase (TAL1).
3. Ribulose 5 phosphate epimerase (RPE1).
4. Trans-ketolase (TKL1).
5. Ribose 5 phosphate isomerase (RKI1)

In addition to these genes, the KanMX selection cassette surrounded by loxP sites was included as a part of the *E. coli-S. cerevisiae* shuttle vector pUG6 (Güldener U, Heck S, Fielder T, Beinhauer J, Hegemann J H. "*A new efficient gene disruption cassette for repeated use in budding yeast.*" NAR 1996, 24:2519-24).

Figure 3:
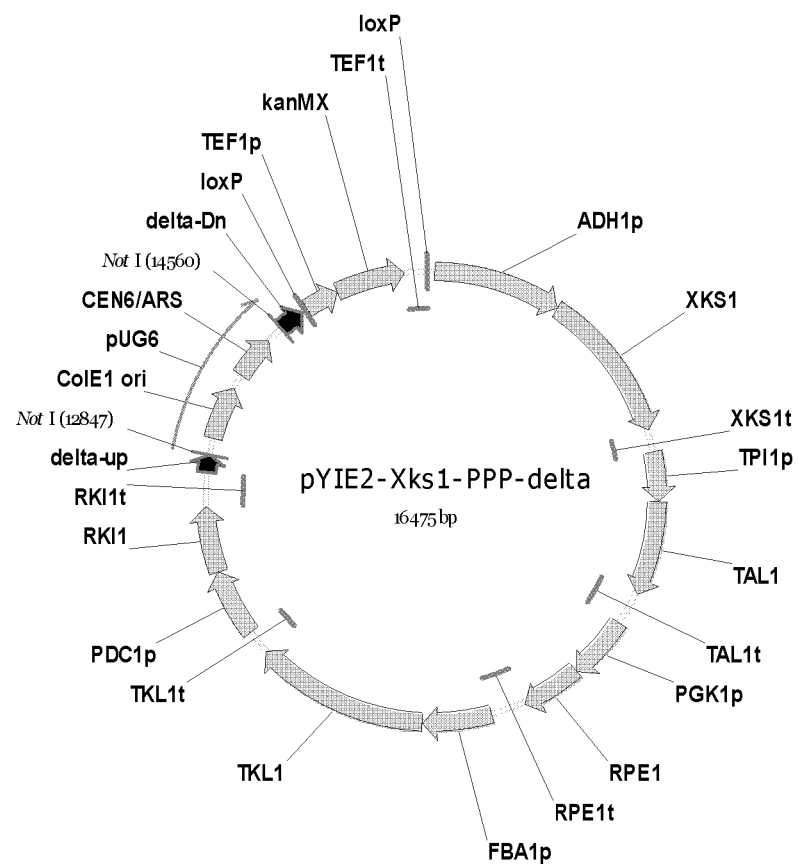
FIG. 3 shows a map of the resulting plasmid pYIE2-XKS1-PPP-δ.

A map of the resulting plasmid pYIE2-XKS1-PPP-δ is shown in FIG. 3. A table listing the genetic elements used is shown below:

| Base position (bp) | Size (bp) | Genetic element | Description | Origin |
|---|---|---|---|---|
| 1-1500 | 1500 | ADH1p | Yeast ADH1 promoter | *Saccharomyces cerevisiae* |
| 1501-3303 | 1803 | XKS1 | Xylulo kinase | *Saccharomyces cerevisiae* |
| 3303-3563 | 260 | XKS1t | Xylulo kinase terminator | *Saccharomyces cerevisiae* |
| 3564-4149 | 586 | TPI 1p | Yeast TPI promoter | *Saccharomyces cerevisiae* |
| 4150-5257 | 1108 | TAL1 | Trans-aldolase | *Saccharomyces cerevisiae* |

-continued

| Base position (bp) | Size (bp) | Genetic element | Description | Origion |
|---|---|---|---|---|
| 5258-5657 | 400 | TAL1t | Trans-aldolase terminator | Saccharomyces cerevisiae |
| 5658-6407 | 750 | PGK1p | Yeast PGK promoter | Saccharomyces cerevisiae |
| 6408-7124 | 717 | RPE1 | Ribulose 5 phosphate epimerase | Saccharomyces cerevisiae |
| 7125-7524 | 400 | RPE1t | Ribulose 5 phosphate epimerase terminator | Saccharomyces cerevisiae |
| 7525-8344 | 820 | FBA1p | Yeast FBA promoter | Saccharomyces cerevisiae |
| 8345-10387 | 2043 | TKL1 | Trans-ketolase | Saccharomyces cerevisiae |
| 10387-10667 | 280 | TKL1t | Trans-ketolase terminator | Saccharomyces cerevisiae |
| 10668-11467 | 800 | PDC1p | Yeast PDC promoter | Saccharomyces cerevisiae |
| 11468-12444 | 777 | RKI1 | Ribose 5 phosphate isomerase | Saccharomyces cerevisiae |
| 12445-12644 | 400 | RKI1t | Ribose 5 phosphate isomerase terminator | Saccharomyces cerevisiae |
| 12645-12844 | 200 | Delta up | Delta DNA upstream sequence | Saccharomyces cerevisiae |
| 12845-14565 | 1720 | pUG6 | E. coli vector including ColE1 origin for E. coli replication and CEN6/ARS replication origin for yeast replication | Escherichia coli |
| 14566-14865 | 300 | Delta Dn | Delta DNA downstream sequence | Saccharomyces cerevisiae |
| 14866-14907 | 82 | Linker | Synthetic linker | Synthetic DNA |
| 14908-14941 | 34 | loxP | Lox recombination site | Bacteriophage P1 |
| 14942-15339 | 398 | TEF1p | A. gossypii TEF promoter | Ashbya gossypii |
| 15340-16149 | 810 | KanMX | Kanamycin (G418) resistance marker | Escherichia coli |
| 16150-16414 | 256 | TEF1t | A. gossypii TEF terminator. | Ashbya gossypii |
| 16415-16448 | 34 | loxP | Lox recombination site | Bacteriophage P1 |
| 16449-16475 | 27 | Linker | Synthetic linker | Synthetic DNA |

The plasmid pYIE2-XKS1-PPP-δ was digested with NotI and the vector elements were removed by agarose gel electrophoresis. The linear fragment containing all of the expression cassettes were then transformed into CIBTS0916 for double homologous recombination followed by selection for kanamycin (G418) resistance. A kanamycin resistant colony was selected and termed CIBTS0931.

CIBTS0931 contains both the zeocin selection marker and the kanamycin selection marker. Both of them are flanked with loxP recombination sites.

In order to remove the zeocin and kanamycin resistance markers the strain was transformed with the episomal plasmid pSH47-hyg again, and transformants were selected on plates containing hygromycin. Subsequently, screening for transformants that had lost zeocin and kanamycin resistance was performed and after that screening for a strain that also lost the hygromycin resistance marker was done. A strain CIBTS1000 was selected and shown to have lost the plasmid pSH47-hyg.

Example 2

Adaptation of the Strain CIBTS1000 to High Xylose Uptake and Acetate Resistance

The strain CIBTS1000 was modified so that it could utilize xylose as a carbon source and ferment it to ethanol. However the xylose utilization was very inefficient. A well-known way to improve that in the field of metabolic engineering is to use adaptation. This was also done in this case. The strain CIBTS1000 was serially transferred from shake-flask to shakeflask in a medium containing xylose as sole carbon source and yeast growth inhibitors known to be present in cellulosic biomass hydrolysates. During these serial transfers mutations are accumulated that enable the strain to grow better under the conditions provided—and thereby to utilize xylose better.

In a first round of adaptation, CIBTS1000 was serially transferred in a shake flask system using YPX medium (10 g/l Yeast extract, 20 g/l peptone and 20 g/l xylose) and YPDX (10 g/l Yeast extract, 20 g/l peptone 10 g/l glucose and 10 g/l xylose)

In a second round of adaptation serial transfer was done in YPXI (YPX supplemented with 43 mM sodium formate, 50 mM sodium acetate and 100 mM sodium sulphate) and YPDXI (YPDX supplemented with 43 mM sodium formate, 50 mM sodium acetate and 100 mM sodium sulphate).

In a final round of adaptation serial transfer was done using NREL dilute acid pretreated corn stover hydrolysate (see Example 3) supplemented with 10 g/l Yeast extract, 20 g/l peptone, 10 g/l glucose and 10 g/l xylose.

A strain named CIBTS1260-J132-F3 was selected as an adapted strain.

Example 3

Figure 4:
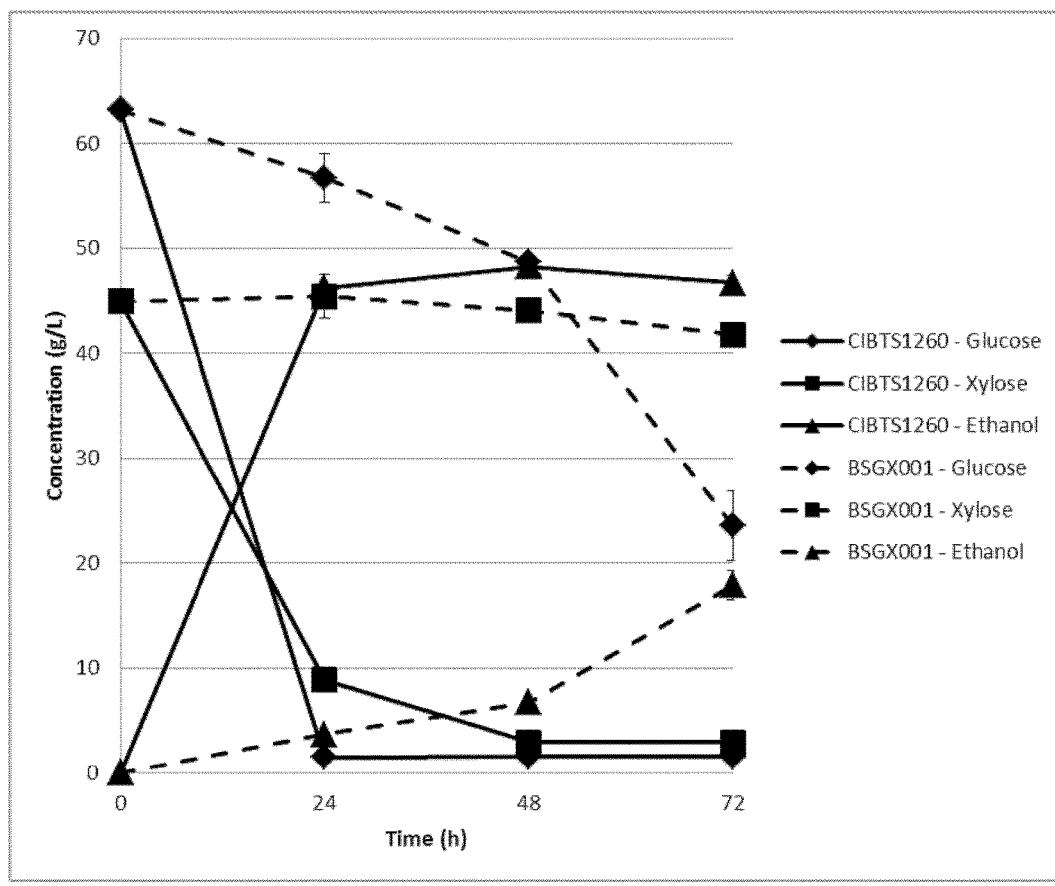
FIG. 4 shows a fermentation comparison of CIBTS1260 versus BSGX001 in NREL Acid Pretreated Corn Stover Hydrolysate at 1 g DCW/L yeast pitch, 35° C., pH 5.5, in 72 hours.

Fermentation Comparison of CIBTS1260 and BSGX001 in NREL Dilute Acid Pretreated Corn Stover Hydrolysate Two Saccharomyces cerevisiae strains, CIBTS1260 and BSGX001, were tested in NREL dilute acid pretreated corn stover hydrolysate (4% w/w sulfuric acid at 180° C. for 5 minutes). The hydrolysate was produced after 3 days of hydrolysis in a 20 kg reactor at 50° C. with 20 mg enzyme protein/g glucan of Cellulolytic Enzyme Composition CA. The dilute acid pretreated corn stover hydrolysate had a final composition of 63.2 g/L glucose, 44.9 g/L xylose, 0.8 g/L glycerol, and 9.5 g/L acetate. Prior to fermentation, each strain was propagated in a 30° C. air shaker at 150 rpm on YPD medium (10 g/L yeast extract, 20 g/L peptone, and 20 g/L glucose). After 24 hours of growth, these two yeast strains were tested in 50 ml of hydrolysate in 125 ml baffled Erlenmeyer flasks at a yeast pitch of 1 g dry cell weight (DCW)/L. Rubber stoppers equipped with 18 gauge blunt fill needles were used to seal each flask, and the flasks were placed in a 35° C. air shaker at a speed of 150 rpm. Samples were taken at 24, 48, and 72 hours for determination of glucose, xylose, and ethanol concentrations via HPLC analysis. The results were averaged for each set of 3 replicates, and are given in FIG. 1 which shows a comparison of CIBTS1260 versus BSGX001 in NREL acid pretreated corn stover hydrolysate at 1 g/L yeast pitch in 72 hours. As shown in FIG. 4, by 48 hours, the CIBTS1260 strain completed full xylose consumption and produced approximately 47 g/L ethanol. The BSGX001 strain, however, was slow to uptake glucose for ethanol conversion and thus consumed only 3 g/L xylose. These results indicate that CIBTS1260 results in improved xylose uptake and utilization for conversion to ethanol compared to BSGX001.

Example 4

Comparison of CIBTS1260 and BSGX001 for Fermentation Performance in Model Media

The fermentation performance of CIBTS1260 and its precursor BSGX001 was compared. Prior to fermentation, each strain was propagated in a 30° C. air shaker at 150 rpm on YPD medium (10 g/L yeast extract, 20 g/L peptone, and 20 g/L glucose). After 24 hours of growth, these two yeast strains were tested in YPX medium (5 g/L yeast extract, 5 g/L peptone, and 50 g/L xylose). To test fermentation performance, each strain was inoculated into 50 ml of YPX medium in 125 ml baffled Erlenmeyer flasks at a yeast pitch of 2 g DCW/L. Rubber stoppers equipped with 18 gauge blunt fill needles were used to seal each flask, and the flasks were placed in a 32° C. air shaker at a speed of 150 rpm. Samples were taken at 24, 48, and 72 hours for determination of glucose, xylose, and ethanol concentrations via HPLC analysis. The results were averaged for each set of 3 replicates, and are given in FIG. 5.

Figure 5:
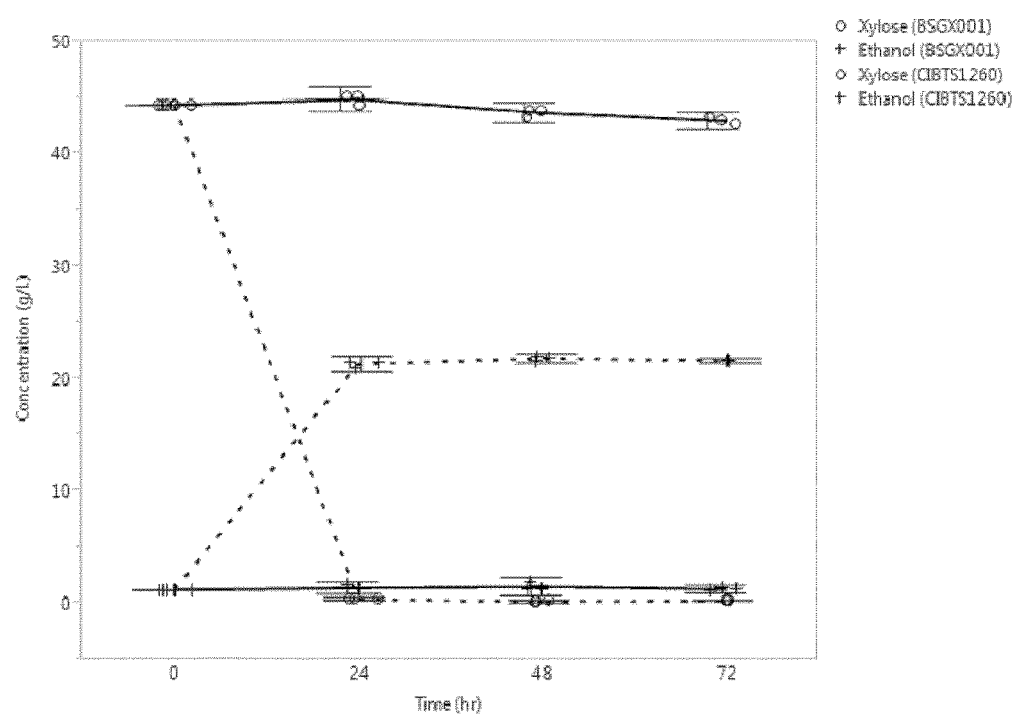
FIG. 5 shows a comparison of *Saccharomyces cerevisiae* vs. BSGX001 in model media: 2/L yeast pitch, 32° C., pH 5.5, 72 hours.

As shown in FIG. 5, CIBTS1260 (dotted lines) has completely utilized all available xylose in 24 hours and produced 21.3 g/L of ethanol. In the 72 hour fermentation time, BSGX001 (solid lines) consumed 1.5 g/L of xylose, and the resulting ethanol concentration was 1.3 g/L.

Example 5

Fermentation of Cellulolytic Enzyme Composition CA ("CA") and Cellulolytic Enzyme Composition CB ("CB") Bagasse Hydrolysate with CIBTS1260

Figure 6:
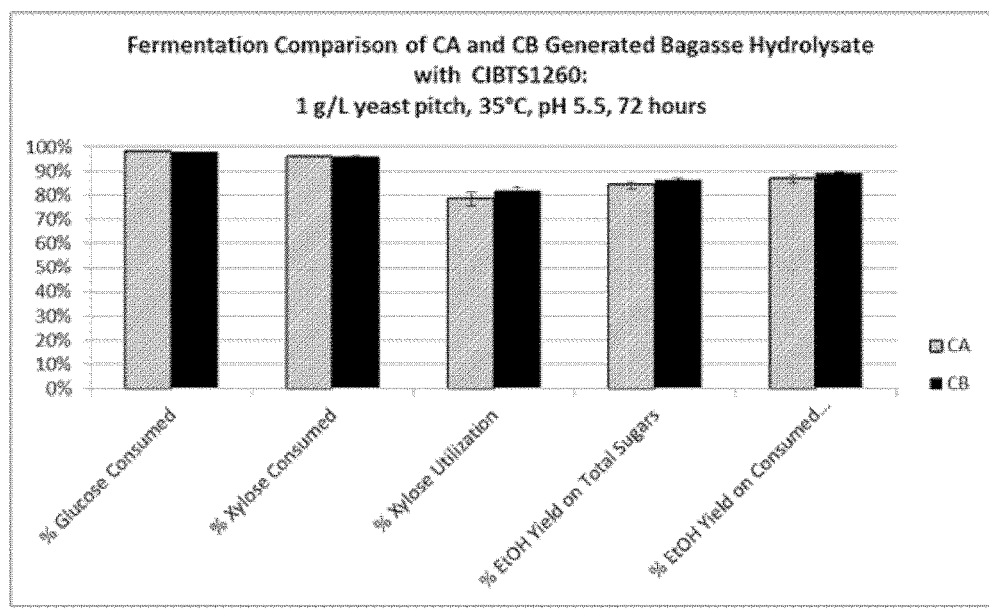
FIG. 6 shows a fermentation comparison of Cellulolytic Enzyme Composition CA and Cellulolytic Enzyme Composition CB generated bagasse hydrolysate with CIBTS1260 at 1 g/L yeast pitch in 72 hours.

CIBTS1260 was used in fermentation tests with NREL dilute acid pretreated bagasse hydrolysates generated at Novozymes North America, USA. The hydrolysate was produced after 5 days of hydrolysis in 2 L IKA reactors at 50° C. with a 6 mg enzyme protein/g glucan dose of two cellulolytic enzyme compositions termed "CA" and "CB". These materials are representative benchmarks for dilute acid pretreated bagasse hydrolysates with final compositions of 40.7 and 58.7 g/L glucose, 42.5 and 44.7 g/L xylose, 0.19 and 0.08 g/L glycerol, and 8.99 and 11.3 g/L acetate for "CA" and "CB", respectively. Prior to fermentation, the yeast were propagated in a 30° C. air shaker at 150 rpm on 2% YPD medium (10 g/L yeast extract, 20 g/L peptone, and 20 g/L glucose). After 24 hours of growth, CIBTS1260 was tested in 50 ml of "CA" and "CB" hydrolysate in 125 ml baffled Erlenmeyer flasks at a yeast pitch of 1 g DCW/L. Rubber stoppers equipped with 18 gauge blunt fill needles were used to seal each flask, and the flasks were placed in a 35° C. air shaker at a speed of 150 rpm. Samples were taken at 24, 48, and 72 hours for determination of glucose, xylose, ethanol, acetate, and glycerol concentrations via HPLC analysis. The results were averaged for each set of 3 replicates, and are given in FIG. 6. Greater than 95% of the glucose and xylose present in both systems was consumed within the 72 hour time period with ethanol yields on total sugars of 84.1% for the "CA" hydrolysate and 86.4% for the "CB" hydrolysate.

Example 6

Figure 7:
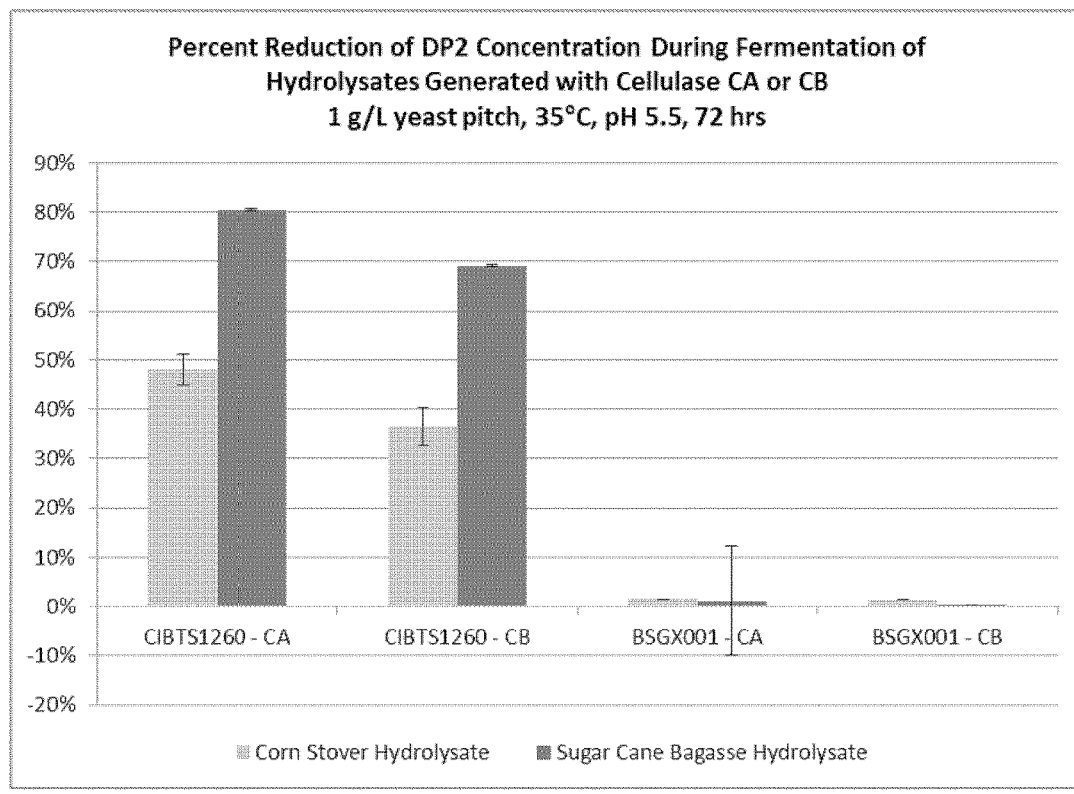
FIG. 7 shows percentage reduction of DP2 concentration during fermentation of hydrolysates generated with Cellulase CA or CB at 1 g/L yeast pitch, 35° C., pH 5.5, 72 hours.

DP2 Reduction During CIBTS1260 and BSGX001 Fermentations of Dilute Acid Pretreated Corn Stover and Sugar Cane Bagasse Hydrolysates Dilute acid pretreated corn stover and sugar cane bagasse from National Renewable Energy Laboratory (NREL), USA, were hydrolysed with a 6 mg enzyme protein/g glucan dose of two enzyme product cocktails termed CA and CB for 5 days in 2 L IKA reactors at 50° C. Prior to fermentation, the CIBTS1260 and BSGX001 yeast were propagated in a 30° C. air shaker at 150 rpm on YPD medium (10 g/L yeast extract, 20 g/L peptone, and 20 g/L glucose). After 24 hours of growth, the cells from each strain were harvested via centrifugation and added to 50 ml of CA and CB hydrolysate supplemented with 2 g/L urea in 125 ml baffled Erlenmeyer flasks at a yeast pitch of 1 g DCW/L (Dry Cell Weight/L), respectively. Rubber stoppers equipped with 18 gauge blunt fill needles were used to seal each flask, and the flasks were placed in a 35° C. air shaker at a speed of 150 rpm. Samples were taken at 0 and 72 hours for determination DP2 concentrations via HPLC analysis. The results were averaged for each set of replicates (n=3 for CIBTS1260 and n=2 for BSGX001). As shown in FIG. 7, in the same hydrolysates, the DP2 concentrations were reduced more for fermentations conducted with CIBTS1260 than for fermentations with BSGX001. The DP2 peak, as measured on HPLC, contains cellobiose and short chain sugars.

The invention claimed is:

1. A process for producing ethanol, comprising:
(a) saccharifying a cellulosic material with a cellulolytic enzyme composition;
(b) fermenting the saccharified cellulosic material with a fermenting microorganism to produce the fermentation product; wherein the fermenting organism is *Saccharomyces cerevisiae* CIBTS1260 (deposited under Accession No. NRRL Y-50973 at the Agricultural Research Service Culture Collection (NRRL), Illinois 61604 U.S.A.).

2. The process of claim 1, comprising recovering the fermentation product from the fermentation.

3. The process of claim 1, wherein the cellulosic material is add pretreated before saccharification.

4. The process of claim 1, wherein the cellulolytic enzyme composition comprises one or more enzymes selected from a cellulase, an AA9 polypeptide, a hemicellulase, a CIP, an esterase, an expansin, a ligninolytic enzyme, an oxidoreductase, a pectinase, a protease, and a swollenin.

5. The process of claim 1, wherein steps (a) and (b) are performed simultaneously in a simultaneous saccharification and fermentation (SSF).

6. The process of claim 1, wherein steps (a) and (b) are performed sequentially (SHF).

7. A recombinant fermenting organism having properties that are the same as that of *Saccharomyces cerevisiae* CIBTS1260 (deposited under Accession No. NRRL Y-50973 at the Agricultural Research Service Culture Collection (NRRL), Illinois 61604 U.S.A.).

8. The fermenting organism of claim 7, wherein the fermenting organism is capable of full xylose consumption by 48 hours fermentation at 1 g Dry Cell Weight/L, 35° C., pH 5.5.

9. The fermenting organism of claim 7, wherein the fermenting organism provides full glucose consumption by 24 hours fermentation at 1 g Dry Cell Weight/L, 35° C., pH 5.5.

10. The fermenting organism of claim 7, wherein the fermenting organism provides more than 30 g/L ethanol after 48 hours fermentation at 1 g Dry Cell Weight/L, 35° C., pH 5.5.

* * * * *